US012714725B2

(12) United States Patent
Dupont et al.

(10) Patent No.: US 12,714,725 B2
(45) **Date of Patent: *Aug. 25, 2026**

(54) STABILIZATION OF SELENITE IN A NUTRITIONAL SOLUTION BY DISSOLVED OXYGEN

(71) Applicants: BAXTER INTERNATIONAL INC., Deerfield, IL (US); BAXTER HEALTHCARE SA, Glattpark (CH)

(72) Inventors: Caroline Dupont, Ixelles (BE); Zouaoui Bourezg, Braine l'Alleud (BE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 1064 days.

This patent is subject to a terminal disclaimer.

(21) Appl. No.: 17/784,325

(22) PCT Filed: Dec. 17, 2020

(86) PCT No.: PCT/EP2020/086678

§ 371 (c)(1),
(2) Date: Jun. 10, 2022

(87) PCT Pub. No.: WO2021/122923

PCT Pub. Date: Jun. 24, 2021

(65) Prior Publication Data

US 2023/0068577 A1 Mar. 2, 2023

(30) Foreign Application Priority Data

Dec. 17, 2019 (EP) .................................... 19217162

(51) Int. Cl.

| | |
|---|---|
| ***A61K 31/198*** | (2006.01) |
| ***A61K 9/00*** | (2006.01) |
| ***A61K 9/08*** | (2006.01) |
| ***A61K 9/48*** | (2006.01) |
| ***A61K 9/50*** | (2006.01) |
| ***A61K 9/70*** | (2006.01) |
| ***A61K 33/04*** | (2006.01) |
| ***A61K 47/02*** | (2006.01) |
| ***A61K 47/12*** | (2006.01) |
| ***A61K 47/26*** | (2006.01) |
| ***A61K 47/30*** | (2006.01) |
| ***A61K 47/38*** | (2006.01) |
| ***A61P 13/02*** | (2006.01) |
| ***A61P 13/04*** | (2006.01) |

(52) U.S. Cl.
CPC ................ *A61K 33/04* (2013.01); *A61K 9/08* (2013.01); *A61K 47/02* (2013.01); *A61K 47/12* (2013.01); *A61K 9/0019* (2013.01)

(58) Field of Classification Search
None
See application file for complete search history.

(56) References Cited

U.S. PATENT DOCUMENTS

| | | | | |
|---|---|---|---|---|
| 2003/0065149 A1* | 4/2003 | McGinnis | A61K 38/42 | 206/530 |
| 2006/0283700 A1* | 12/2006 | Bagley | A61K 33/00 | 203/10 |
| 2009/0305965 A1* | 12/2009 | Kang | A61K 9/0019 | 514/1.1 |
| 2010/0092446 A1* | 4/2010 | Sumiyoshi | A61K 9/08 | 514/474 |

FOREIGN PATENT DOCUMENTS

| | | | |
|---|---|---|---|
| CN | 102511815 A | | 6/2012 |
| CN | 103479667 A | | 1/2014 |
| CN | 108498541 A | | 9/2018 |
| PL | 228438 | * | 3/2018 |
| SK | 134893 | * | 5/1994 |
| WO | WO 0193910 | * | 12/2001 |
| WO | WO2006010410 | | 2/2006 |
| WO | WO2010067251 | | 6/2010 |

OTHER PUBLICATIONS

Stockhausen "Selenium in Total Prenteral Nutrition" 1987.*
Stockhause "Selenium in Total Parenteral Nutrition" 1988.*
Pogatschnik "Trace Element Supplementation and Monitoring in the Adult Patient on Parenteral Nutrition" May 2014.*
PCT Search Report and Written Opinion prepared for PCT Application No. PCT/EP2020/086678, completed Mar. 12, 2021.
Baptista, R. J., et al., "Utilizing Selenious Acid to Reverse Selenium Deficiency in Total Parenteral Nutrition Patients," 1984, American Journal of Clinical Nutrition, vol. 39, Nr: 5, pp. 816-820.
Slavik P., et al., "Effect of Supplementation of Sodium Selenite and Selenised Yeast on Pregnancy Rate in Beef Cows with initial severe Selenium Deficiency," 2008, Reproduction in Domestic Animals, Blackwell Wiss, vol. 43,Nr: Suppl. 5, pp. 102-103.
Bahr, K., et al., "Selenium supplementation by selenium yeast and sodium selenite: Analysis of the selenium status as well as risks of deficiency and intoxication." 1999, Laboratoriums Medizin / Journal of Laboratory Medicine, vol. 23, Nr: 11, p. 594-599.

* cited by examiner

*Primary Examiner* — Danah Al-Awadi
(74) *Attorney, Agent, or Firm* — K&L Gates LLP

(57) ABSTRACT

The invention relates to a medical product for preventing or correcting selenium deficiency in a patient comprising a solution provided in a flexible container comprising at least one selenium compound in the form of Se(IV), which is preferably selected from the group consisting of sodium selenite, selenous acid and selenium dioxide, characterized in that the solution comprises dissolved oxygen (DO), preferably 0.5 ppm to 8 ppm DO.

20 Claims, 5 Drawing Sheets

A

B

A

B

STABILIZATION OF SELENITE IN A NUTRITIONAL SOLUTION BY DISSOLVED OXYGEN

CROSS-REFERENCE TO RELATED APPLICATIONS

This application is a national stage entry under 35 U.S.C. § 371 (b) of PCT International Application No. PCT/EP2020/086678, filed Dec. 17, 2020, which claims the benefit of European Patent Application Serial No. 19217162.7, filed on Dec. 17, 2019, the entire disclosures of both of which are incorporated herein by reference.

DESCRIPTION

The invention relates to the field of clinical nutrition, corresponding medical products and nutritional solutions.

The invention relates to a medical product for preventing or correcting selenium deficiency in a patient comprising a solution provided in an oxygen impermeable flexible container comprising selenium as Se(IV), characterized in that the solution comprises dissolved oxygen (DO), preferably 0.5 ppm to 8 ppm DO.

In certain embodiments of the invention, the solution of the medical product of the invention comprises at least one additional trace element. The solution may be ready-to-use and may be contained in one chamber of a multi chamber container having at least two, at least three, at least four, at least five or at least six chambers. Furthermore, the invention relates to a method of preparing a medical product of the invention.

BACKGROUND OF THE INVENTION

Parenteral Nutrition aims to supply nutrients to patients by venous access. Nutrients are composed of macronutrients (lipids, amino acid or protein and dextrose or carbohydrates), micronutrients (vitamins and trace elements) and electrolytes.

Parenteral nutrition, such as in the form of one or more solutions, can be provided in the form of flexible bags, either in the form of single flexible bags containing glucose, amino acids or lipids with or without electrolytes, which can be mixed together prior administration, or multi chamber flexible bags providing separated macronutrients and electrolytes, in a ready to use format. The bags are typically made of a synthetic or plastic material, for example materials such as polypropylene (PP), polyethylene (PE), ethylene vinyl alcohol (EVOH), ethylene-vinyl acetate (EVA) and all possible copolymers, essentially any synthetic material suitable for containing the components to be administered.

In the state of the art, micronutrients are typically added to nutrition bags directly before administration. For this purpose, vitamins can be provided in glass vials in the form of lyophilizates or solutions to be reconstituted and/or mixed into the nutrition/infusion bags. Trace elements are also provided in glass vials or polypropylene ampules meant to be mixed into infusion bags prior to administration.

Prior to usage, referring to the start administering the formulation to the patient, the micronutrients are sometimes added to the mixture or macronutrients via an injection port of the container or bag (septum) or are added via a Y-connector to the infusion line. This process takes time and several handling steps increasing the risk of errors or contamination.

To avoid these potential problems, products have been developed that already contain some trace elements in nutrition multi-chamber bags, such as, for example, Pediaven, a parenteral nutrition binary solution intended for infants, children and adolescents, which contains trace elements in the glucose chamber. However, it has been reported that the trace element selenium, provided as selenium dioxide in the product, is absent in the finished product potentially due to degradation, as announced in July 2014 (http://www.pharmacovigilance-tours.fr/490.html). Another product, Elneopa, from Otsuka Pharmaceuticals, contains certain trace elements in a small dedicated chamber as part of a multi-chamber bag. However, this product does not contain selenium. Flexible multi-chamber container for the preparation of medical mixed solutions have also been described in WO2006/010410A1.

KR10-2019-0105737 relates to an infusion solution preparation containing fat-soluble vitamins and trace elements, and more particularly, to an infusion solution preparation which includes a plurality of chambers therein and thus stores reducing sugars, amino acids, lipids and fat-soluble vitamins, and trace elements separately. The publication, among other trace elements contained in a chamber of a multi-chamber nutritional product, also mentions selenium ions and a preferred concentration of 3 μg/mL to 7.0 μg/ml based on a selenium cation. Specific ions or ways to stabilize such selenium ions in the formulation are not mentioned. Furthermore, WO2010/067251A1, Bahr K et al (*laboratoriumsmedizin* (DE), vol. 23, no. 11, 1999, pages 594-599) and Baptista R J et al (*The American Journal Of Clinical Nutrition*, vol. 39, no. 5, May 1984, pages 816-820) describe selenium containing compositions for nutritional supplementation. Furthermore, Slavik P et al (*Reproduction In Domestic Animals*, vol. 43, no. Suppl. 5, November 2008, pages 102-103) describes the use of sodium selenite for supplementing selenium deficiency.

It is known in the art that selenium, iodine and copper—especially in combination—are difficult to include in nutrition bags, as they can undergo chemical reactions, especially as they have to undergo extreme conditions such as a heat sterilization and extended storage periods (for example, Allwood et al. *Compatibility and Stability of Additives in Parenteral Nutrition Admixtures. Nutrition* 1998, Vol. 14, No. 9, pp. 697-706; Eisenberg et al. *Stability of selenium sources reviewed*. Feedstuffs, Jun. 18, 2012).

Furthermore, in various formulation studies, when attempting to introduce trace elements into nutrition multi-chamber bags, serious stability issues have been experienced, in particular the loss of selenium has been observed. This may be due to the fact that selenium in the form of Se(IV) and specifically in the form of sodium selenite, selenious acid or selenium dioxide is prone to adsorption, for example to plastic materials or iron oxides; can be reduced into metallic selenium in the presence of reducing agents like ascorbic acid; can be reduced into hydrogen selenide, which is a volatile substance; and/or can be transformed into selenious dioxide at low pH, which is also a volatile substance under certain conditions.

In addition to selenium, iodine, fluoride and copper also showed stability issues during formulation trials. Copper is a reactive entity and can catalyse various chemical reactions and it is known that it can precipitate. Iodide can be reduced into iodine, which is potentially volatile. Furthermore, fluoride showed a decreasing concentration over time.

So, while it is possible, under certain conditions such as in Peditrace, Nutryelt or Addaven to stabilize selenium with certain other trace elements in specifically tailored plastic ampoules or glass vials for addition to a parenteral nutrition product as described above, it turned out to be challenging to stabilize it in standard parenteral nutrition products which contain a variety of different compounds in flexible bags, where the container and the conditions cannot readily be adapted to the special requirements of selenium alone or in combination with other trace elements such as, for example, iodine and/or copper, and which in addition will generally have to undergo terminal heat sterilization specifically in the presence of lipid emulsions.

As a consequence of the above, to date there is no ready-to-use medical product for parenteral administration available that comprises a solution for parenteral administration to a patient in need thereof, comprising selenium, and which is stable over a prolonged period of time. Selenium, and potentially also other trace elements, must be manually added to the ready-made solutions shortly before administration. This process is associated with a significant risk of medication error, for example with respect to the amount of the trace elements, or of introducing contamination to the sterilized ready-made products. Contaminations can include potential infectious agents, which represent a serious risk factor to patients in hospitals, especially those receiving nutritional solutions e.g. via parenteral administration.

In light of the prior art, there remains a significant need to develop medical products for preventing or correcting selenium deficiency in a patient that are straightforward, have a reasonable shelf-life and are easy to use, including avoiding additional mixing steps. Due to the instability of selenium in solution, specifically when combined with additional trace elements, such products are not readily available.

SUMMARY OF THE INVENTION

In light of the prior art the technical problem underlying the present invention is to provide a pre-prepared, sterilized medical product for preventing or correcting selenium deficiency in a patient, comprising a ready-to-use formulation for parenteral administration provided in a flexible container and containing selenium. Preferably, the flexible container is made from an oxygen-impermeable material.

This problem is solved by the features of the independent claims. Preferred embodiments of the present invention are provided by the dependent claims.

The invention therefore relates to a medical product for preventing or correcting selenium deficiency in a patient comprising a solution provided in an oxygen-impermeable flexible container for parenteral administration and comprising at least one selenium compound in the form of Se(IV), which is preferably selected from the group consisting of sodium selenite, selenous acid and selenium dioxide, characterized in that the solution comprises dissolved oxygen (DO), preferably 0.5 ppm to 8 ppm DO.

It may be preferable, in certain embodiments of the invention, to target an oxygen range of from 0.5 to 2.0 ppm when in addition to the selenium compound according to the invention other, oxygen-sensitive compounds such as trace elements or vitamins are present in the same compartment as the said selenium. In certain embodiments, an oxygen range of from 1.0 ppm to 2.0 ppm may be preferable for stably formulating compositions according to the invention.

In certain embodiments of the invention, the solution of the medical product of the invention comprises sodium selenite. In some embodiments, the solution of the medical product of the invention comprises selenous acid. In some embodiments, the solution of the medical product of the invention comprises selenium dioxide.

It was surprising that the presence of dissolved oxygen, in particular at the indicated, stable concentration of 0.5 ppm to 8 ppm, leads to the stabilization of sodium selenite, selenous acid and/or selenium dioxide in a solution which is otherwise protected from the interchange of gases with its surrounding, because it is generally expected that oxygen is involved in redox reactions and is often deleterious for macro- and micronutrient stability in solution. In particular, certain trace elements and vitamins have been reported to be sensitive to the presence or absence of oxygen when stored in sealed containers, such as in sealed flexible bags.

However, the present invention is based on the finding that the presence of a stable and controlled concentration of dissolved oxygen in a solution comprising sodium selenite, selenous acid and/or selenium dioxide alone or in combination with further sensitive trace elements, such as iodine and/or copper, leads to stabilization of these selenium containing compounds which are known to be unstable in solution and in particular when present in sealed medical nutritional products which are generally provided in oxygen-impermeable containers to avoid the above-mentioned redox reactions. Specifically, while oxygen-permeable containers are known, such as used, for example, for Peditrace™, and which allow gas exchange between the interior of the container and the surrounding air, most parenteral products are provided in oxygen-impermeable containers due to the redox sensitivity of the nutritional components contained. Oxygen-permeable containers, on the other hand, will not provide for a defined, stable oxygen concentration which was found to be a prerequisite for providing long-term stability especially of a highly sensitive composition of various trace elements.

As used herein the solution of the medical product of the invention comprising rising at least one selenium compound in the form of Se(IV), which is preferably selected from the group consisting of sodium selenite, selenous acid and selenium dioxide, may also be referred to as “the selenium solution”, “the solution comprising/containing selenium”, or “the solution comprising/containing Se(IV)”.

In the context of the present invention, it is understood that the wording “stable (and controlled) concentration of dissolved oxygen in a solution of 0.5 ppm to 8 ppm” relates to a DO concentration that remains in the range of 0.5 ppm and 8 ppm throughout shelf-life of the medical product of the invention, wherein 8 ppm corresponds about to oxygen saturation of the solution of the invention. In other words, it is not necessary that the exact oxygen concentration of the solution in the medical product remains stable, but it is required that throughout shelf life the concentration does not drop below this range, namely below 0.5 ppm. Accordingly, in preferred embodiments of the invention, the DO concentration in the solution is at least 0.5 ppm DO.

In embodiments, the DO in the Se(IV)-containing solution is at least 0.5 ppm during shelf life. In embodiments, the DO in the Se(IV)-containing solution does not fall below 0.5 ppm throughout shelf life of the medical product.

In preferred embodiments, the DO in the Se(IV)-containing solution at the time of filling (and optionally sealing) of the solution in the flexible container and before sterilization is at least 6 ppm. In embodiments, the DO concentration in the solution at the time of filling and before sterilization is from 6 ppm to 8 ppm (wherein 8 ppm corresponds about to the oxygen saturation level of the solution).

In preferred embodiments, an oxygen tight sealed chamber of the flexible container comprising the selenium solution comprises a headspace of a gas composition comprising oxygen. In other words, in such embodiments the chamber of the flexible container comprising the selenium solution comprises additionally a volume of a gas composition comprising oxygen. It is understood that such an additional gas volume or "headspace" is a space or volume within a sealed chamber that is not filled with the solution, i.e. a volume filled with air/gas left at the top of a filled container before sealing. Generally, headspace would be avoided or minimized to the extent possible regarding potentially unwanted interactions between the gas included therein (ambient air) and the liquid (or solid) content of the container (see, for example, US20030110736A1). In contrast, in the context of the present invention such headspace can be intentionally used and designed to be sufficient for stocking oxygen, for example via the ambient air, so that consumed oxygen can be replaced and the DO in the solution can be maintained above 0.5 ppm throughout intended shelf-life. Using a headspace according to the invention, i.e. providing for a sufficient gas reservoir including, for example ambient air and or any other gas or gas mixture that might be consumed in the solution of a gas- or oxygen impermeable bag or a chamber thereof is a general principle which can be used also in connection with other compounds that require a certain level of gas, such as, for example, oxygen, for prolonged stability in situations where gas is consumed by one or more components of the solutions stored in the bag or chamber of an MCB or where there is a risk of loss of such gas, e.g. through the primary container or any port tube, for example.

In preferable embodiments, the gas composition comprising oxygen is ambient air, which comprises about 78% nitrogen, 21% oxygen, about 1% of other gases. However, in embodiments the gas composition comprising oxygen may be an oxygen enriched gas composition that may even be composed of almost only oxygen, especially in cases where the headspace volume should be reduced. In embodiments, the gas composition of the headspace may comprise from 10-100% oxygen, such as 5, 6, 7, 8, 9, 10, 11, 12, 13, 14, 15, 16, 17, 18, 19, 20, 21, 22, 23, 24, 25, 26, 27, 28, 29, 30, 0 31, 32, 33, 34, 35, 36, 37, 38, 39, 40, 42, 44, 46, 48, 50, 54, 58, 62, 66, 70, 75, 80, 85, 90, 95, 96, 97, 98, or 99% oxygen.

In case of ambient air, the volume of the headspace is preferably in the range of about 40% of the volume of the selenium solution comprised in the chamber. For example, in case of 25 ml of selenium solution preferably comprising about 70 μg of selenium, the headspace may be 10 ml. However, in embodiments the volume of the headspace may be in the range of 10-80% of the volume of the selenium solution, such as 11, 12, 13, 14, 15, 16, 17, 18, 19, 20, 21, 22, 23, 24, 25, 26, 27, 28, 29, 30, 0 31, 32, 33, 34, 35, 36, 37, 38, 39, 40, 42, 44, 46, 48, 49, 50, 55, 60, 65, 70, 75 or 80% of the volume of the selenium solution. For example, in case of 25 ml of selenium solution sealed in a chamber of the flexible container, the headspace may be in the range of 2.5 ml to 12.5 ml, preferably about 3-12 ml, such as 3, 4, 5, 6, 7, 8, 9, 10 or 11 ml. The skilled person can calculate corresponding volumes of headspace based on this disclosure in case of other volumes of the selenium solution.

As mentioned before, the volume of the headspace may be adjusted accordingly if a different gas composition is used. For example, in case of a gas with enriched oxygen content, a smaller headspace can be used, as is evident to the skilled person and can be calculated on the basis of the above ratios indicated for ambient air.

In embodiments of the medical product of the invention, the DO according to the invention stabilizes the sodium selenite, selenous acid and/or selenium dioxide, alone or in combination with other trace elements, in the solution for at least three months when stored at a broad temperature range of between 1 and 50° C. It was unexpected that comparative experiments could demonstrate that the listed selenium containing compositions were stabilized in solution during various temperatures tested in the range of from 1 to 50° C. for prolonged periods in an oxygen-impermeable flexible container, such as at least three months.

In embodiments, the DO according to the invention stabilizes the sodium selenite, selenous acid and/or selenium dioxide alone or in the presence of other trace elements in the solution for at least three months when stored at up to 40° C. Furthermore, in embodiments said DO stabilizes the sodium selenite, selenous acid and/or selenium dioxide alone or in the presence of other trace elements in the solution for at least six months when stored at up to 40° C.

In further embodiments of the invention, the DO stabilizes the sodium selenite, selenous acid and/or selenium dioxide alone or in the presence of other trace elements in the solution for at least 6 months, preferably for at least 12 months, more preferably for at least 18 months, most preferably for at least 24 months.

In further embodiments of the invention, the DO stabilizes the sodium selenite, selenous acid and/or selenium dioxide alone or in the presence of other trace elements in the solution for least 6 months, preferably 12 months, more preferably 18 months, most preferably 24 months, at a temperature of up to 30° C.

In yet further embodiments of the invention, the DO stabilizes the sodium selenite, selenous acid and/or selenium dioxide alone or in the presence of other trace elements in the solution for least 6 months, preferably for at least 12 months, more preferably for at least 18 months, most preferably for at least 24 months, at a temperature of from about 18° C. to 25° C.

In still further embodiments of the invention, the DO according to the invention stabilizes the sodium selenite, selenous acid and/or selenium dioxide alone or in the presence of other trace elements in the solution for least 6 months, preferably for at least 12 months, more preferably for at least 18 months, most preferably for at least 24 months, at a regular storage temperature, including for example, but without limitation thereto, of temperatures of room temperature, varying from 15-30° C., more preferably 18-25° C., or storage in refrigerated conditions, such as from 1 to 10° C., preferably 2 to 8, or 3 to 7° C.

In embodiments of the invention, the solution of the medical product is a sterilized solution. In some embodiments, the solution of the medical product of the invention may be sterile.

It is an important advantage that the solution of the present invention can be sterilized after preparation and packaging into a flexible bag prepared from an oxygen-impermeable material that may be sealed airtight and liquid tight without a significant loss of the trace elements provided therein such as in particular sodium selenite, selenous acid and/or selenium dioxide alone or in the presence of other trace elements. In certain embodiments, the solution of the invention undergoes terminal heat sterilisation after preparation of and filling the solution into the flexible container. Sterilisation may occur prior to or after filling of the solution into the flexible bag of the medical product of the invention, wherein terminal sterilisation, specifically heat sterilisation of the filled and sealed flexible container is preferable.

It is highly preferable that the container or the chamber of the container containing the selenium comprising solution is able to stabilize the DO content between 0.5 and 8 ppm.

According to the invention, this can be realized in different ways, such as, for example, by making use of an oxygen impermeable film material where an oxygen adsorber are added to the primary pouch, such as in cases where other formulations contained in the product, e.g. in a MCB product, require the absence of oxygen. It is also possible to use a semi-permeable film material together with an oxygen-impermeable secondary or outer packaging in cases where no oxygen adsorber is required. Both approaches can be used in and are applicable for embodiments of the flexible container wherein medical ports or filling ports are used. Such ports should preferably be attached or sealed into the container in a way that ensures the chamber containing the solution comprising Se(IV) is sealed in an oxygen tight manner, to the extent possible. An inevitable loss of oxygen, for example, through the port seals where oxygen absorbers are used, can be addressed according to the invention with an appropriate headspace used as a reservoir of e.g. oxygen to assure the stability of Se(IV) for the intended shelf-life. In embodiments, the chamber comprising the solution containing selenium comprises a port that is essentially oxygen impermeable.

Sterilisation may be done by a terminal heat sterilisation process but also by using terminal filtration, gamma irradiation or any other sterilization technique. Also, the solution of the medical product of the invention may be filled into the flexible bag by an aseptic filling process ensuring that no contamination of the essentially sterile solution occurs during filling and before sealing of the flexible bag. In some embodiments, the solution may have been sterilized, but is not necessarily sterile. For example, a sterilisation treatment may have been conducted, but an absolute sterility may not be achieved and/or required.

In the context of the invention the terms "flexible bag" and "flexible container" may be used interchangeably. The terms "solution" and "formulation" are also used interchangeably in the context of the present invention.

In further embodiments, the concentration of DO in the solution is equal or above 0.5 ppm, more preferably equal or above 1.0 ppm. In embodiments, the concentration of the DO is not higher than 4 ppm. In embodiments the DO is higher than 0.8 ppm and not higher than 2 ppm.

In embodiments of the invention, the concentration of DO in the solution may be any value in the range of 0.5, 0.75 or 1 to 2 ppm or 0.5, 0.75, 1 or 2 to 8 ppm, such as 0.5, 0.75, 1, 1.5, 2, 2.5, 3, 3.5, 4, 4.5, 5, 5.5, 6, 6.5, 7, 7.5 or 8 ppm. The indicated ranges include the noted end-values. Ranges comprising any combination of disclosed values are considered as embodiments of the invention.

In embodiments, the concentration of DO in the solution is equal or above 0.5 ppm, more preferably equal or above 1.0 ppm, throughout shelf life of the medical product.

In embodiments of the invention, the DO in the Se(IV) containing solution is at least 0.5 ppm throughout shelf life of the medical product of the invention. In embodiments the DO concentration in the solution can decrease during shelf life but remains above 0.5 ppm. For example, it is preferable that the DO concentration of the solution is above 6 ppm at the time of filling of the solution into the flexible container and before sterilization. During sterilization and storage, the DO concentration may decrease over time, but does not fall below 0.5 ppm throughout shelf life.

In embodiments of the medical product of the invention, the concentration of DO in the solution at the time of filling and preferably sealing of a chamber of the flexible container comprising the solution is at least 6 ppm.

In embodiments, it is possible that the oxygen concentration in the selenium containing solution decreases within the medical product after filling, sealing and sterilization and during shelf life of the product, even if the chamber comprising the solution is completely oxygen impermeable. In embodiments, the oxygen of the solution may be consumed during shelf life by compounds which may be present in the Se(IV) containing solution which may lead to a decrease in the oxygen concentration in the formulation comprising Se(IV). While such oxygen consumption may generally be no issue or may even be intentional, it is preferable for a Se(IV) comprising formulation that at the time of filling and sealing the selenium solution within a chamber of the medical product, the oxygen concentration is at least 6 ppm, such as in the range of 6 ppm to 8 ppm. Such a high oxygen concentration at the time of filling and sealing ensures that during shelf life of the product the oxygen concentration does not fall below 0.5 ppm, meaning that even if oxygen consumption in the chamber occurs, the DO concentration does not sink below 0.5 ppm and the Se(IV) remains stable.

In embodiments, a sealed chamber of the flexible container comprising the solution comprising at least one selenium compound in the form of Se(IV) additionally comprises a headspace of a gas composition comprising oxygen.

In preferred embodiments, a flexible container or a chamber thereof which comprises the solution containing at least one selenium compound in the form of Se(IV) additionally comprises a headspace of a gas composition comprising oxygen, and the sealed chamber is oxygen impermeable, and the DO in the solution at the time of filling and preferably sealing of the chamber is at least 6 ppm. It was shown that in such embodiments the DO in the solution is or remains equal to or above 0.5 ppm throughout shelf life of the medical product.

As used herein, the term "shelf life" relates to the time that the medical product of the invention can be stored at defined storage conditions after sealing and sterilizing. Depending on the storage conditions, shelf life may vary.

It is a great advantage that a content of DO according to the invention is suitable for stabilizing the selenium containing compounds alone and especially also in combination with other sensitive trace elements in the context of the medical product of the invention since such DO concentrations can be easily established without complicated technical instrumentation or manipulation of the solution.

In some embodiments, the solution of the medical product comprises sodium selenite. The use of sodium selenite in the context of the present invention is particularly advantageous since it was found that this compound is stable in products according to the invention that comprise a stable, predetermined DO concentration of above 0.5 ppm, specifically from 0.5 ppm to 8 ppm, whereas it has been observed that in the absence of stable amount of DO in the said range sodium selenite is instable and cannot be detected or can only be detected at significantly decreased concentrations after storage for more than 1-3 months.

In further embodiments, the medical product according to the invention has an acidic pH, preferably in the range of from 1 to 4, more preferably from 2 to 3.5, more preferably from about 2.5 to 3.2. It is a particular advantage of the solution of the present invention that sodium selenite, selenous acid and/or selenium dioxide are stable in the presence of from 0.5 to 8 ppm DO, and specifically also in the presence of from 0.8 ppm to 4 ppm DO or in the presence of from 1 ppm to 2 ppm, not only at about neutral pH in the range of 7 to 7.5, but also at acidic pH. The selenium in a product according to the invention is in particular also stable at acidic pH, such as a pH in the range of 1-4, 1.5-3.5, 1.8-3.2, 2-3, 2.1-2.9, 2.2-2.8, 2.3-2.7, 2.4-2.6 and about 2.5. The indicated ranges include the noted end-values. Ranges comprising any combination of disclosed end-values are considered as embodiments of the invention.

The stability at such acidic pH conditions is important, in particular if the solution also includes other trace elements that may not be stable at neutral pH, but only under acidic conditions. This is in particular the case for iodide (I), which has been reported to be more stable in solutions with acidic pH. However, this may also be the case for nutritional solutions comprising one or more of the trace elements copper (Cu), zinc (Zn), iron (Fe), manganese (Mn), chromium (Cr), fluoride (F) and molybdenum (Mo), some of which are also sensitive towards oxygen.

In embodiments of the invention, the solution comprises an acid, preferably an organic acid selected from the group comprising malic acid, tartaric acid, citric acid, maleic acid, fumaric acid, and more preferably malic acid, wherein the concentration of the organic acid is preferably in the range of from 100 mM to 400 mM, preferably from 190 mM to 220 mM, and more preferably about 200 mM.

In another embodiment, the solution comprises an acid, preferably an organic acid selected from the group consisting of malic acid, tartaric acid, citric acid, maleic acid, fumaric acid, and more preferably malic acid, wherein the concentration of the organic acid is preferably in the range of from 50 mM to 400 mM, preferably from 100 mM to 200 mM.

In another embodiment, the solution comprises malic acid. In embodiments the solution comprises malic acid at a concentration in the range of from 100 mM to 400 mM, preferably from 190 mM to 220 mM, such as, for example, 140 to 180 mM or 160 mM to 200 mM. The use of malic acid in the context of a nutritional medical product is particularly advantageous since it is an organic acid that naturally occurs in fruits, such as apples, apricots, blackberries, blueberries, cherries, grapes, peaches and others and is particularly well tolerated by human subjects when administered in the context of a nutritional product.

The acid concentration in the solution of the medical product of the invention can be in any range that leads to a suitable pH value for the desired application. Depending on the acid, slightly different concentrations may be required to achieve, for example, an acidic pH value in the range of 1-4. A person skilled in the art can choose and adjust appropriately a suitable acid concentration for a preferred embodiment comprising a solution of a given pH and a specific acid.

In embodiments of the medical product of the invention, the solution does not comprise macronutrients. Preferably such macronutrients are selected from the group comprising carbohydrates, proteins and lipids, and wherein preferably the solution does not comprise any other nutrients.

In further embodiments the solution does not comprise carbohydrates.

In further embodiments the solution does not comprise proteins or amino acids, besides optionally those comprising selenium. In embodiments the solution does not comprise lipids. In embodiments the solution does not comprise electrolytes. In embodiments the solution does not comprise vitamins. In embodiments the solution does not comprise other trace elements other than selenium. In embodiments the solution only contains trace elements. In embodiments the solution contains selenium as the only trace element. In embodiments the solution contains selenium as the only nutrient. In embodiments the solution contains selenium as the only nutrient, besides water (in case water is considered as a nutrient).

In embodiments, the solution of the medical product of the invention comprises at least one additional trace element, preferably selected from the group comprising zinc, iron, copper, manganese, chromium, iodine, fluoride and molybdenum.

In embodiments, the solution of the medical product of the invention comprises at least one additional trace element, preferably selected from the group comprising zinc, iron, manganese and/or copper.

In embodiments, the solution of the medical product of the invention comprises at least one additional trace element, preferably selected from the group consisting of zinc, iron, copper, manganese, chromium, iodine, fluoride and molybdenum. In embodiments, the solution of the medical product of the invention comprises at least one additional trace element, preferably selected from the group consisting of zinc, iron, manganese and/or copper.

In embodiments, the solution of the medical product of the invention comprises as additional trace elements at least zinc, iron, manganese and copper. In embodiments, the solution of the medical product of the invention comprises as additional trace elements at least zinc, iron, manganese, copper, chromium, iodine, fluoride and molybdenum.

In embodiments, the solution of the medical product of the invention comprises as additional trace elements at least zinc, iron, manganese, copper and chromium. In embodiments, the solution of the medical product of the invention comprises as additional trace elements at least zinc, iron, manganese, copper and iodine. In embodiments, the solution of the medical product of the invention comprises as additional trace elements at least zinc, iron, manganese, copper and fluoride. In embodiments, the solution of the medical product of the invention comprises as additional trace elements at least zinc, iron, manganese, copper and molybdenum.

In embodiments, the solution of the medical product of the invention comprises as additional trace elements at least zinc, iron, manganese, copper, chromium and iodine. In embodiments, the solution of the medical product of the invention comprises as additional trace elements at least zinc, iron, manganese, copper, chromium and fluoride. In embodiments, the solution of the medical product of the invention comprises as additional trace elements at least zinc, iron, manganese, copper, chromium and molybdenum.

In embodiments, the solution of the medical product of the invention comprises as additional trace elements at least zinc, iron, manganese, copper, iodine and fluoride. In embodiments, the solution of the medical product of the invention comprises as additional trace elements at least zinc, iron, manganese, copper, iodine and molybdenum.

In embodiments, the solution of the medical product of the invention comprises as additional trace elements at least zinc, iron, manganese, copper, fluoride and molybdenum.

In embodiments, the solution of the medical product of the invention comprises as additional trace elements at least zinc, iron, manganese, copper, chromium, iodine and fluoride. In embodiments, the solution of the medical product of the invention comprises as additional trace elements at least zinc, iron, manganese, copper, chromium, iodine and molybdenum. In embodiments, the solution of the medical product of the invention comprises as additional trace elements at least zinc, iron, manganese, copper, chromium, fluoride and molybdenum. In embodiments, the solution of the medical product of the invention comprises as additional trace elements at least zinc, iron, manganese, copper, iodine, fluoride and molybdenum.

In the context of the invention, zinc can be provided as any suitable compound, such as a salt, such as preferably gluconate, chloride or sulfate. In the context of the invention, iron can be provided as any suitable compound, such as a salt, such as preferably gluconate, chloride or sulfate. In the context of the invention, copper can be provided as any suitable compound, such as a salt, such as preferably gluconate, chloride or sulfate. In the context of the invention, manganese can be provided as any suitable compound, such as a salt, such as preferably gluconate, chloride or sulfate. In the context of the invention, chromium can be provided as any suitable compound, such as a salt, such as preferably gluconate, chloride or sulfate. In the context of the invention, iodine can be provided as any suitable compound, such as a salt, such as preferably potassium or sodium iodide. In the context of the invention, fluoride can be provided as any suitable compound, such as a salt, such as preferably potassium or sodium fluoride. In the context of the invention, molybdenum can be provided as any suitable compound, such as a salt, such as preferably gluconate, chloride or sulfate.

Furthermore, embodiments of the invention relate to a medical product, wherein the solution is administered parenterally. In further embodiments, the solution of the medical product of the invention is administered or consumed orally. In embodiments, the solution can be administered enterally.

In the context of the present invention, the solution of the claimed medical product can comprise sodium selenite, selenous acid and/or selenium dioxide in an amount corresponding to 10-200 μg, preferably 40-100 μg, more preferably about 70 μg of selenium.

In embodiments, the amount of selenium in the solution of the medical product corresponds to a recommended daily dose (dd) of selenium, wherein a daily dose may be quantified as the mass of selenium to be administered to a patient per day, for example μg of selenium per patient per day (μg/patient/day). In embodiments, the amount of selenium in the solution of the product may be in the range of 1-500, 2-450, 4-400, 6-350, 7-300, 8-270, 9-235, 10-200, 15-190, 20-180, 25-170, 30-160, 35-150, 40-140, 45-130, 50-120, 52-115, 54-110, 56-105, 58-100, 60-95, 62-90, 64-88, 66-86, 68-84, 70-82, 72-80, 74-78 or 76 μg selenium. The indicated ranges include the noted end-values. Ranges comprising any combination of disclosed end-values are considered as embodiments of the invention.

In the context of the solution of the invention, selenium is provided as sodium selenite, selenous acid and/or selenium dioxide. Accordingly, for example, when 70 μg of selenium are provided in form of sodium selenite ($Na_2O_3Se$), which has a molar mass 172.95 g/mol, wherein selenium has a molar mass of 78.97 g/mol, this corresponds to about 153.2 μg sodium selenite.

Accordingly, when 70 μg of selenium are provided in form of selenous acid ($H_2SeO_2$ or more accurately described as $(HO)_2SeO$), which has a molar mass 128.97 g/mol, wherein selenium has a molar mass of 78.97 g/mol, this corresponds to about 114.32 μg selenous acid.

Furthermore, when 70 μg of selenium are provided in form of selenium dioxide ($SeO_2$), which has a molar mass 110.96 g/mol, wherein selenium has a molar mass of 78.97 g/mol, this corresponds to about 98.36 μg selenium dioxide.

As evident from these examples, a skilled person is able to calculate the amount of a compound comprising selenium in a solution of a medical product of the invention on the basis of the molar mass of said compound and the amount of selenium present in the solution. In the same way, it is possible to calculate the amounts of compounds comprising other trace elements on the basis of the molar mass of the respective trace element and compound comprising said trace element.

In embodiments, the medical product of the invention represents a daily nutritional dose for a patient. Accordingly, the amounts of the components of the product, such as the selenium in the solution of the product, are calculated and provided in order to cover a daily dose of a patient for said compound. Depending of the volume of the solution of the product and the amount of selenium, the concentration of selenium in the solution can be calculated.

In embodiments of the medical product of the invention, the solution in the oxygen-impermeable flexible container has a volume of about 25 ml. In such an embodiment, the amount of selenium in the solution can be 70 μg, and the resulting concentration of selenium can be 2.8 μg/ml (or 2.8 mg/l). Se-concentration ranges can be calculated on the basis of the amounts of Se disclosed herein. Preferred Se-concentrations of the invention are in the range of 0.28-28 mg/l. However, the Se-concentration may also be in the range of 0.1-100 mg/l, 0.2-90, 0.3-85, 0.4-80, 0.5-75, 0.6-70, 0.7-65, 0.8-60, 0.9-55, 1-50, 1.2-48, 1.4-46-1.6-44, 1.8-42, 2-40, 2.2-38, 2.4-36, 2.6-34, 2.8-32, 3-30, 3.5-29, 4-28, 4.5-27, 5-26, 5.5-25, 6-24, 6.5-23, 7-22, 7.5-21, 8-20, 9-19, 10-18, 11-17, 12-16, 13-15 or 14 mg/ml. The indicated ranges include the noted end-values. Ranges comprising any combination of disclosed end-values are considered as embodiments of the invention.

The following Table 1 indicates suitable ranges and preferred amounts for adults of trace elements that can be comprised by the medical product and in particular by the solution of the medical product of the invention. Ranges and amounts for pediatrics may be different and can be adapted according to the applicable recommendations. Such suitable ranges can be updated from time to time, so any preferred amounts of trace elements that can be comprised in a medical product according to the invention may be adapted to recommendations currently in force.

TABLE 1

Suitable amounts and ranges of amounts of trace elements that can be used in the context of the invention. Indicated ranges are based on different ranges recommended in the art. The amounts refer to a medical product of the invention that provides one daily dose for one patient. The indicated ranges include the noted end-values. Ranges comprising any combination of disclosed end-values are considered as embodiments of the invention.

| Trace element | ESPEN 2009 [17] | DGEM 2009 [24] | ASPEN 2012 [13] | AuSPEN 2014 [40] | Consensus paper 2019 [41] | Preferred amount #1 | Preferred amount #2 |
|---|---|---|---|---|---|---|---|
| Zinc (μg) | 2500-5000 | 2500-4000 | 3000-5000 | 3200-6500 | 2500-6500 | 5000 | 5000 |
| Iron (μg) | 1000-1200 | 1000-1500 | — | 1100 | 1000-1200 | 1000 | NA |
| Copper (μg) | 300-500 | 300-1200 | 300-500 | 317-508 | 300-610 | 300 | 300 |
| Manganese (μg) | 200-300 | 200-800 | 55 | 55 | 55-100 | 55 | 55 |
| Chromium (μg) | 10-15 | 10-20 | 10-15 | 10-15 | 10-15 | 10 (or NA) | NA |
| Selenium (μg) | 20-60 | 20-80 | 60-100 | 60-100 | 20-100 | 70 | 60 |
| Iodine (μg) | 100 | — | — | 126 | 70-150 | 100 | NA |
| Fluoride (μg) | 1000 | — | — | — | — | 1000 | NA |
| Molybdenum (μg) | 20 | — | — | 19 | No recommendation | 20 | NA |

Table 2 indicates suitable concentration ranges for adults of trace elements that can be comprised by the solution of the medical product of the invention. Ranges for pediatrics may be different and can be adapted according to the applicable recommendations. Such suitable ranges can be updated from time to time, so any preferred amounts of trace elements that can be comprised in a medical product according to the invention may be adapted to recommendations currently in force.

TABLE 2

Suitable concentrations and concentration ranges of trace elements (TE) that can be used in the context of the solution of the medical product of the invention. Indicated ranges refer to the preferred daily dose of a patient as listed in Table 1 and volumes of 2.5 to 250 ml of the solution. Se(IV) as mentioned in this Table encompasses sodium selenite, selenous acid and/or selenium dioxide.

| TE | Method LOQ mg/L | Chemical Form | Chemical form; Solubility in water | Batch 1 concentration (mg/L; 1 dd/ 250 m1) | Batch 2 concentration (mg/L; 1 dd/ 25 ml) | Batch 3 concentration (mg/L; 1 dd/ 2.5 ml |
|---|---|---|---|---|---|---|
| Zn | 3.5 | Cl | 4.32 kg/L | 20 | 200 | 2000 |
| Cu | 0.350 | Cl, 2H2O | 706 g/L | 1.2 | 12 | 120 |
| Mn | 0.025 | Cl, 4H2O | 634 g/L | 0.22 | 2.2 | 22 |
| F | 5 | Na | 50 g/L | 8 | 80 | 800 |
| I | 0.080 | K | 1.48 kg/L | 0.4 | 4 | 40 |
| Mo | 0.014 | Na, 2H2O | <840 g/L | 0.08 | 0.8 | 8 |
| Cr | 0.014 | Cl, 6H2O | 585 g/L | 0.04 | 0.4 | 4 |
| Fe | 0.350 | Cl, 6H2O | 920 g/L | 4 | 40 | 400 |
| Se | 0.035 | Na, Se (IV) | >100 g/L | 0.28 | 2.8 | 28 |

In the context of the medical product of the invention, the volume of the solution comprising sodium selenite, selenous acid and/or selenium dioxide can be in the range of 1-1000 ml, 1.5-980, 2-960, 2.5-940, 3-920, 3.5-900, 4-880, 4.5-860, 5-840, 6-820, 7-800, 8-780, 9-760, 10-740, 12-720, 14-700, 16-680, 18-660, 20-640, 22-620, 24-600, 26-580, 28-560, 30-540, 32-520, 34-500, 36-480, 34-460, 36-440, 38-420, 40-400, 45-490, 50-480, 55-470, 60-460, 65-450, 70-440, 85-430, 90-420, 95-410, 100-400, 110-390, 120-380, 130-370, 140-360, 150-350, 160-340, 170-330, 180-320, 190-310, 200-300, 210-290, 220-280, 230-270, 240-260 or 250 ml. The indicated ranges include the noted end-values. Ranges comprising any combination of disclosed end-values are considered as embodiments of the invention.

In embodiments of the invention, the solution is contained in one chamber of a multi-chamber container having at least two, at least three, at least four, at least five or at least six chambers.

In embodiments, the container comprises at least a first chamber containing a carbohydrate formulation, a second chamber containing an amino acid formulation, a third chamber containing a lipid formulation, optionally comprises electrolytes and/or vitamins in at least the first, second and/or third chamber, and wherein at least one chamber comprises sodium selenite, selenous acid and/or selenium dioxide in the presence of from 0.5 ppm to 8 ppm oxygen.

In embodiments, the container comprises at least a first chamber containing a carbohydrate formulation, a second chamber containing an amino acid formulation, a third chamber containing a lipid formulation, comprises electrolytes and/or vitamins in at least the first, second and/or third chamber, and wherein at least one chamber comprises sodium selenite, selenous acid and/or selenium dioxide in the presence of from 0.5 ppm to 8 ppm oxygen.

In embodiments, the container comprises at least a first chamber containing a carbohydrate formulation, a second chamber containing an amino acid formulation, a third chamber containing a lipid formulation, comprises electrolytes and/or vitamins in a fourth and/or fifth chamber and sodium selenite, selenous acid and/or selenium dioxide in the presence of from 0.5 ppm to 8 ppm oxygen in a further chamber, optionally together with other trace elements.

In embodiments, the container comprises at least a first chamber containing a carbohydrate formulation, a second chamber containing an amino acid formulation, a third chamber containing a lipid formulation, wherein the solution comprising sodium selenite, selenous acid and/or selenium dioxide in the presence of from 0.5 ppm to 8 ppm dissolved oxygen (DO) is present in a fourth chamber.

In embodiments of the invention, the solution is contained in one chamber of a multi chamber container having at least two, at least three, at least four, at least five or at least six chambers, wherein the solution comprises sodium selenite. In embodiments of the invention, the container is made from an oxygen-impermeable, flexible material. In further embodiments, the solution comprising sodium selenite comprises further trace elements and 0.5 to 3 ppm DO.

In certain embodiments comprising the container with at least a first chamber containing a carbohydrate formulation, a second chamber containing an amino acid formulation, a third chamber containing a lipid formulation, the solution comprises sodium selenite. In embodiments of the invention, the container is made from an oxygen-impermeable, flexible material.

In embodiments of the invention, the solution is prepared by dissolving sodium selenite, selenous acid and/or selenium dioxide in a liquid medium. In preferred embodiments, the liquid medium is water, preferably ultrapure water (UPW; also called deionized (DI) water) or water for injection. UPW water has organic particles and dissolved gases removed. Water for injection is water of extra high quality without significant contamination.

The invention further relates to a method of preparing a medical product for preventing or correcting selenium deficiency in a patient according to any one of the preceding claims, wherein the solution is prepared by the steps comprising a. dissolving sodium selenite, selenous acid and/or selenium dioxide in a liquid medium, preferably water for injection, to produce a solution, with a concentration of selenium between 0.28 and 28 mg/L,
b. optionally further dissolving, alone or together with sodium selenite, selenous acid and/or selenium dioxide, an acid, preferably an organic acid selected from the group comprising malic acid, tartaric acid, citric acid, maleic acid and fumaric acid, and/or at least one additional trace element selected from the group comprising zinc, iron, copper, manganese, chromium, iodine, fluoride and molybdenum,
c. adjusting the solution to a concentration of dissolved oxygen of from 0.5 ppm to 8 ppm,
d. sterilizing the solution, preferably by heat sterilization.

Sterilizing of the solution may occur prior or after filling the solution into a flexible container of the invention.

Preferably, sterilization of the solution occurs after filling of the solution into the flexible container or a chamber of a flexible multi-chamber container and sealing the solution in the container.

In preferred embodiments of the method of the invention, the DO concentration in the solution is adjusted to at least 6 ppm, such as 6-8 ppm, at the time of filling the solution into the flexible bag.

The optional method step of dissolving an acid may be used for adjusting the pH of the solution to an acidic pH.

Furthermore, in embodiments of the method of the invention at least one additional trace element, preferably selected from the group consisting of zinc, iron, copper, manganese, chromium, iodine, fluoride and molybdenum is added to the solution.

The invention further relates to a sterile or sterilized solution for parenteral administration comprising at least one compound selected from the group comprising sodium selenite, selenous acid and selenium dioxide for use in preventing or correcting selenium deficiency in a patient, characterized in that the solution comprises dissolved oxygen (DO).

Furthermore, the invention relates to a method of preventing or correcting selenium deficiency in a patient, the method comprising administering a solution comprising at least one compound selected from the group consisting of sodium selenite, selenous acid and selenium dioxide to said patient, wherein the solution comprises dissolved oxygen (DO).

In embodiments of the method of preventing or correcting selenium deficiency in a patient according to the present invention the method comprises administering the solution for maintaining plasma selenium levels and preventing depletion of endogenous stores in a patient receiving total parenteral nutrition.

In the context of the method of preventing or correcting selenium deficiency in a patient, the patients are adult patients. In embodiments, the patients are pediatric patients, such as neonates, infants, children or adolescents.

As used herein, the term "adult" refers to persons of 20 years of age and older. The term "pediatric" refers to neonates, including premature (pre-term), full term, and post-mature neonates of up to one month of age; infants of between one month and one year of age; children of between one and up to 12 years of age, and adolescents of between 13 and up to 19 years of age.

All features disclosed in the context of the medical product for preventing or correcting selenium deficiency in a patient of the invention also relate to the method of preparing such a medical product and are herewith disclosed also in the context of the method of preparing the medical product and the other way around. The same holds true for the sterile or sterilized solution of the invention and the method of preventing or correcting selenium deficiency in a patient according to the present invention.

DETAILED DESCRIPTION OF THE INVENTION

All cited documents of the patent and non-patent literature are hereby incorporated by reference in their entirety.

The present invention is directed to a sterilized medical product for preventing or correcting selenium deficiency in a patient comprising a solution provided in an oxygen-impermeable flexible container comprising at least one compound selected from the group comprising or consisting of sodium selenite, selenous acid and selenium dioxide, characterized in that the solution comprises 0.5 ppm to 8 ppm dissolved oxygen (DO) at 20° C. to 25° C.

As disclosed herein, the term medical product relates to any product intended to be used for medical purposes, preferably for clinical nutrition. The medical product of the invention is intended and designed for the medical purpose of preventing or correcting selenium deficiency in a patient.

Selenium deficiency refers to a condition of a patient who does not have enough selenium in his body. This can cause several health problems. The patient group of the invention comprises all patients or patient groups that are at risk of developing a selenium deficiency or have already developed a selenium deficiency. In particular, the medical product of the invention is intended to correct or treat a selenium deficiency that has already occurred in a patient. Furthermore, the invention may be used to prevent the occurrence of selenium deficiency in patients at risk of or suspected of developing a selenium deficiency, for example due to severely compromised intestinal function, total or partial parenteral nutrition, gastrointestinal bypass surgery, or advanced age. In the present context of the invention, prevention is considered to encompass both absolute prevention, i.e. stopping of a disease developing at all, and/or a preventive measure that lowers the risk or likelihood of the patient developing the unwanted medical conditions or slows or delays the development, first occurrence and/or progression of the disease.

Selenium is a chemical element with the symbol Se and atomic number 34. It is a nonmetal (more rarely considered a metalloid) with properties that are intermediate between the elements above and below in the periodic table, sulfur and tellurium, and also has similarities to arsenic. Selenium itself exists in a variety of chemical forms including selenite and selenate as well as elemental selenium and it is often found associated with sulfur-containing compounds. Selenium is a component of the amino acids selenocysteine and selenomethionine. Very small quantities of selenium are required to maintain proper health in both animals and humans and this selenium must be obtained through dietary sources. There are around 25 seleno-proteins in humans and many of these are enzymes that act to protect the body against oxidative damage. Without selenium, the function of the selenium-requiring proteins can be compromised which results in the signs and symptoms of deficiency. Since the ageing process, as well as certain diseases, including cancer and cardiovascular disease, are associated with an increase in oxidative damage, maintaining adequate selenium intake may provide some protection against these processes.

In humans, selenium is a trace element nutrient that functions as cofactor for glutathione peroxidases and certain forms of thioredoxin reductase. Selenium-containing proteins are produced from inorganic selenium via the intermediacy of selenophosphate ($PSeO_3^{3-}$).

Selenium deficiency can occur in patients with severely compromised intestinal function, such as those undergoing total parenteral nutrition, patients undergoing CRRT, cancer patients, preterm infants, patients staying in an ICU for a prolonged time, those who have had gastrointestinal bypass surgery, and in those of advanced age (over 90). These patients are at risk of developing selenium deficiency. Also, people dependent on food grown from selenium-deficient soil are at risk. Increased risk for developing various diseases has also been noted, even when certain individuals lack optimal amounts of selenium, but not enough to be classified as deficient.

The medical product of the invention can be used in the treatment of patients having, developing or being at risk of developing selenium deficiency. The treatment can aim to prevent or correct a selenium deficiency in this patient group.

Selenium deficiency, which may be defined by low (<60% of normal) selenoenzyme activity levels in brain and endocrine tissues, occurs when a low selenium level is linked with an additional stress, such as high exposures to mercury or increased oxidant stress from vitamin E deficiency. Selenium deficiency as used herein can also occur in healthy well-nourished individuals. Selenium deficiency in combination with Coxsackievirus infection can lead to Keshan disease, which is potentially fatal and represents a specific form of selenium deficiency in the sense of the invention. Selenium deficiency also contributes (along with iodine deficiency) to Kashin-Beck disease, which is another selenium deficiency in the sense of the invention. The primary symptom of Keshan disease is myocardial necrosis, leading to weakening of the heart. Kashin-Beck disease results in atrophy, degeneration and necrosis of cartilage tissue. Keshan disease also makes the body more susceptible to illness caused by other nutritional, biochemical, or infectious diseases. Selenium is also necessary for the conversion of the thyroid hormone thyroxine (T4) into its more active counterpart triiodothyronine (T3). Therefore, selenium deficiency can cause symptoms of hypothyroidism, including extreme fatigue, mental slowing, goiter, cretinism, and recurrent miscarriage.

The U.S. Institute of Medicine (IOM) updated Estimated Average Requirements (EARs) and Recommended Dietary Allowances (RDAs) for selenium in 2000. If there is not sufficient information to establish EARs and RDAs, an estimate designated Adequate Intake (AI) is used instead. The current EAR for selenium for people ages 14 and up is 45 μg/day. The RDA is 55 μg/day. RDAs are higher than EARs so as to identify amounts that will cover people with higher than average requirements. RDA for pregnancy is 60 μg/day. RDA for lactation is 70 μg/day. For children ages 1-13 years the RDA increases with age from 20 to 40 μg/day. As for safety, the IOM sets Tolerable upper intake levels (ULs) for vitamins and minerals when evidence is sufficient. In the case of selenium the UL is 400 μg/day. Collectively the EARs, RDAs, AIs and ULs are referred to as Dietary Reference Intakes (DRIs) [Institute of Medicine (2000). "Selenium". Dietary Reference Intakes for Vitamin C, Vitamin E, Selenium, and Carotenoids. Washington, DC: The National Academies Press. pp. 284-324]. The European Food Safety Authority (EFSA) refers to the collective set of information as Dietary Reference Values, with Population Reference Intake (PRI) instead of RDA, and Average Requirement instead of EAR. AI and UL defined the same as in United States. For women and men ages 15 and older the AI is set at 70 μg/day. AI for pregnancy is 70 μg/day, for lactation 85 μg/day. For children ages 1-14 years the AIs increase with age from 15 to 55 μg/day. These AIs are higher than the U.S. RDAs [EFSA, Overview on Dietary Reference Values for the EU population as derived bythe EFSA Panel on Dietetic Products, Nutrition and Allergies (NDA), September 2017]. The European Food Safety Authority (EFSA) reviewed the same safety question and set its UL at 300 μg/day, which is lower than the U.S. value [EFSA, "Tolerable Upper Intake Levels For Vitamins And Minerals", February 2006].

In the context of the invention, the medical product comprises a flexible container or bag, preferably made from an oxygen-impermeable material, comprising at least one compound selected from the group consisting of sodium selenite, selenous acid and selenium dioxide, characterized in that the solution comprises 1 ppm to 8 ppm dissolved oxygen (DO).

Sodium selenite is the inorganic compound with the formula $Na_2SeO_3$. This salt is a colorless solid. The pentahydrate $Na_2SeO_3(H_2O)_5$ is the most common water-soluble selenium compound. Selenous acid (or selenious acid) is the chemical compound with the formula $H_2SeO_3$. Structurally, it is more accurately described by $H_2SeO_3$. It is the principal oxoacid of selenium; the other being selenic acid. Selenium dioxide is the chemical compound with the formula $SeO_2$ and is a colorless solid. It is one of the most frequently encountered compounds of selenium.

The term "dissolved oxygen" (DO) refers to the level of free, non-compound oxygen present in water or other liquids or solutions, such as solutions for parenteral nutrition. Oxygen saturation (symbol $SO_2$) is a relative measure of the concentration of oxygen that is dissolved or carried in a given medium as a proportion of the maximal concentration that can be dissolved in that medium. It can be measured with a dissolved oxygen probe such as an oxygen sensor or an optode in liquid media, usually water.

Dissolved oxygen is usually reported in milligrams per liter (mg/L) or as a percent of air saturation. However, studies also report DO in parts per million (ppm) or in micromoles (μmol). 1 mg/L is equal to 1 ppm. The relationship between mg/L and % air saturation varies with temperature, pressure and salinity of the water. One micromole of oxygen is equal to 0.022391 milligrams. Thus 100 μmol/L $O_2$ is equal to 2.2 mg/L $O_2$. To calculate dissolved oxygen concentrations from air saturation, it is necessary to know the temperature and salinity of the sample. Barometric pressure has already been accounted for as the partial pressure of oxygen contributes to the percent air saturation. Salinity and temperature can then be used in Henry's Law to calculate what the DO concentration would be at 100% air saturation. However, it is easier to use an oxygen solubility chart. These charts show the dissolved oxygen concentration at 100% air saturation at varying temperatures, and salinities. This value can then be multiplied by the measured percent air saturation to calculate the dissolved oxygen concentration [Fondriest Environmental, Inc. "Dissolved Oxygen." Fundamentals of Environmental Measurements. 19 Nov. 2013.].

Oxygenation of liquids occurs for example through exposure of the liquids to gases containing oxygen. For example, exposure of a liquid sample to the atmosphere comprising around 21% $O_2$ leads to oxygenation through diffusion of the gaseous oxygen into the liquid. This process can be accelerated for example by stirring, flushing the liquid with an oxygen-containing gas or similar techniques known to the skilled person.

There are several methods available in the art for measuring dissolved oxygen concentrations. Modern techniques involve either an electrochemical or optical sensor, where the dissolved oxygen sensor is attached to a meter for spot sampling and laboratory applications or to a data logger, process monitor or transmitter for deployed measurements and process control. An example is the fiber-optic oxygen meter Microx TX3 from PreSens Precision Sensing GmbH (Germany) for gaseous and dissolved $O_2$. The colorimetric method offers a basic approximation of dissolved oxygen concentrations in a sample. There are two methods designed for high-range and low-range dissolved oxygen concentrations. These methods are quick and inexpensive for basic projects but limited in scope and subject to error due to other redoxing agents that may be present in the water. The traditional method is the Winkler titration.

In embodiments of the invention, the solution of the medical product is a sterilized solution. In the context of the invention, the term "sterilized" relates to a solution that has undergone a process of sterilization. Sterilization refers to any process that eliminates, removes, kills, or deactivates all forms of life (in particular referring to microorganisms such as fungi, bacteria, viruses, spores, unicellular eukaryotic organisms such as Plasmodium, etc.) and other biological agents like prions present in a specific surface, object or fluid, for example food or biological culture media. Sterilization can be achieved through various means, including heat, chemicals, irradiation, high pressure, and filtration. Sterilization is distinct from disinfection, sanitization, and pasteurization, in that those methods reduce rather than eliminate all forms of life and biological agents present. After sterilization, an object is referred to as being sterile or aseptic.

According to one embodiment of the invention, sterilization is done by heat. According to another embodiment of the invention, sterilization involves heating under pressure in the presence of water to generate steam; this method is recommended by various pharmacopeias. Generally, said steam sterilization is performed in an autoclave and can be used for drug products, medical devices, plastic bags and other single-use equipment, glass containers, surgical dressings and more.

Other methods encompass sterilization with moist heat. The term "moist heat" as used herein includes the use of saturated steam, steam air and hot water cascade or water spray sterilization. According to one embodiment of the invention, sterilization with moist heat is preferable.

Sterilization can also be achieved via dry heating. Much higher temperatures (180-200° C.) are required for this method. Dry heating is commonly used to sterilize glassware, metal and other surfaces.

Exposure to radiation is another sterilization method used throughout the industry. Gamma radiation is the most common, though other options include infrared and ultraviolet radiation and high-velocity electrons. Radiation is typically used for the sterilization of single-use components/systems, but it can be used for packaged drug products.

Treatment with gases is also a sterilization alternative. Such gases include ethylene oxide, formaldehyde, glutaraldehyde, propylene oxide, hydrogen peroxide and chlorine dioxide. This method is more commonly used to sterilize clean-room suites. Sterilization via filtration is the only option if the other processes are not suitable for the specific product or component. In filtration, the final drug product solution is passed through a filter that has been produced under aseptic manufacturing conditions and designed with appropriate pore sizes/surface chemistries that remove bacteria via size exclusion, entrapment, electrostatic attraction and other modalities.

In embodiments of the invention, the solution comprises an acid, preferably an organic acid selected from the group comprising malic acid, tartaric acid, citric acid, maleic acid, fumaric acid, more preferably malic acid.

As used herein, a nutrient is a substance used by an organism, such as a human, to survive, grow, and reproduce. Nutrients can be incorporated into cells for metabolic purposes or excreted by cells to create non-cellular structures, such as hair, scales, feathers, or exoskeletons. Some nutrients can be metabolically converted to smaller molecules in the process of releasing energy, such as for carbohydrates, lipids, proteins/amino acids, and fermentation products (ethanol or vinegar), leading to end-products of water and carbon dioxide. All organisms require water. Essential nutrients for animals and humans are the energy sources, some of the amino acids that are combined to create proteins, a subset of fatty acids, vitamins and certain minerals/trace elements.

A classification used primarily to describe nutrient needs of animals divides nutrients into macronutrients and micronutrients. Consumed in relatively large amounts, macronutrients (carbohydrates, lipids/fats, proteins/amino acids, water) are used primarily to generate energy or to incorporate into tissues for growth and repair. Micronutrients are needed in smaller amounts; they have subtle biochemical and physiological roles in cellular processes, like vascular functions or nerve conduction. Inadequate amounts of essential nutrients, or diseases that interfere with absorption, result in a deficiency state that compromises growth, survival and reproduction.

Macronutrients comprise carbohydrates, proteins, lipids, and water. Macronutrients are defined as a class of chemical compounds which humans consume in the largest quantities and which provide humans with the bulk of energy. While water does make up a large proportion of the total mass ingested as part of a normal diet, it does not provide any nutritional value. Carbohydrates comprise glucose, sucrose, ribose, amylose (a major component of starch), amylopectin, maltose, galactose, fructose, lactose. Proteins are composed of amino acids comprising standard amino acids alanine, arginine, aspartic acid (aspartate), asparagine, cysteine, glutamic acid (glutamate), glutamine, glycine, histidine, isoleucine (branched chain amino acid), leucine (branched chain amino acid), lysine, methionine, phenylalanine, proline, serine, threonine, tryptophan, tyrosine, valine (branched chain amino acid). Lipids (or fats) comprise saturated fats such as butyric acid (C4), caproic acid (C6), caprylic acid (C8), capric acid (C10), lauric acid (C12), myristic acid (C14), pentadecanoic acid (C15), palmitic acid (C16), margaric acid (C17), stearic acid (C18), arachidic acid (C20), behenic acid (C22), lignoceric acid (C24), cerotic acid (C26); monounsaturated fats such as myristol, pentadecanoic, palmitoyl, heptadecenoic, oleic acid, eicosen, erucic acid, nervonic acid; polyunsaturated fats such as linoleic acid (LA)—an essential fatty acid, α-Linolenic acid (ALA)—an essential fatty acid, stearidonic acid (SDA), arachidonic acid (ETA), timnodonic acid (EPA), clupanodonic acid (DPA), cervonic acid (DHA); essential fatty acids, such as α-Linolenic acid ALA (18:3) Omega-3 fatty acid and Linoleic acid LA (18:2) Omega-6 fatty acid, being the starting point for other important omega-acids (e.g. DHA, EPA).

Micronutrients are essential elements required by human in small quantities throughout life to orchestrate a range of physiological functions to maintain health, in particular vitamins and dietary minerals/trace elements. Trace elements/trace minerals/dietary minerals include Boron, Cobalt (as a component of vitamin B12), Fluoride, Chromium, Copper, Iodine, Iron, Manganese, Molybdenum, Selenium and Zinc.

In the context of the medical product of the invention, trace elements may be provided as chloride or sodium salts, such as zinc chloride, iron chloride, copper chloride, sodium selenite, manganese chloride, sodium fluoride, potassium iodide, chromium chloride, sodium molybdate.

Vitamins comprise Vitamin B complex, Vitamin B1 (thiamin), Vitamin B2 (riboflavin), Vitamin B3 (niacin), Vitamin B5 (pantothenic acid), Vitamin B6 group (Pyridoxine, Pyridoxal-5-Phosphate, Pyridoxamine), Vitamin B7 (biotin), Vitamin B9 (folate), Vitamin B12 (cobalamin), Choline, Vitamin A (e.g. retinol (see also—provitamin A carotenoids)), Vitamin C (Ascorbic acid), Vitamin D (vitamin D2 (Ergocalciferol), vitamin D3 (Cholecalciferol)), Vitamin E (tocopherols and tocotrienols), Vitamin K (Vitamin K1 (phylloquinone), Vitamin K2 (menaquinone)).

Electrolytes, such as sodium, potassium, chloride, calcium, magnesium, phosphate and bicarbonate may also be classified as nutrients.

The medical product of the invention comprises a solution provided in a flexible container comprising at least one compound selected from the group consisting of sodium selenite, selenous acid and selenium dioxide, characterized in that the solution comprises 1 ppm to 8 ppm dissolved oxygen (DO). The medical product may comprise further solutions comprising nutrients, such as macronutrients and micronutrients. The solutions of the medical product may be reconstituted before administration to a patient. Administration of the one or more solutions of the product, potentially after reconstitution of the one or more solutions, can occur through various routes of administration, such as parenterally, orally or enterally.

As used herein, "reconstituted solution" refers to a solution for parenteral administration, which is generated by admixing the content of the chambers of a multi-chamber container before use.

Parenteral administration is preferred in the context of the invention. Parenteral nutrition (PN) is the feeding of specialist nutritional products to a person intravenously, bypassing the usual process of eating and digestion. It is called total parenteral nutrition (TPN) or total nutrient admixture (TNA) when no significant nutrition is obtained by other routes, and partial parenteral nutrition (PPN) when nutrition is also partially enteric. It may be called peripheral parenteral nutrition (PPN) when administered through vein access in a limb rather than through a central vein as central venous nutrition (CVN). Enteral food administration is via the human gastrointestinal tract and contrasts with parenteral administration.

In the context of the medical product of the invention, the solution is provided in a flexible container. In embodiments of the invention, the solution is contained in one chamber of a multi chamber container having at least two, at least three, at least four, at least five or at least six chambers.

As used herein, the term "flexible container" refers to a container or bag made of a flexible material, such as bags made from plastic films. The term does not encompass polymeric rigid or semi-rigid containers.

Flexible containers or bags of the invention can be made of materials comprising, without limitation, polyvinyl chloride (PVC), polypropylene (PP), polyethylene (PE), ethylene vinyl alcohol (EVOH), ethylene-vinyl acetate (EVA) and all possible copolymers, essentially any synthetic material suitable for containing the components to be administered.

Oxygen impermeable flexible containers are made of gas barrier films that block oxygen migration to the outside of the container. Different technologies have been developed in order to provide oxygen barrier to transparent films, such as PE films or polyethylene terephthalate films. The main technologies are the following: (1) Coating with high barrier materials, generally inorganic oxide layers (e.g. SiOx or $Al_2O_3$); (2) Multilayer films, wherein an inner layer consists a barrier material such as EVOH, polyamide, aluminum, halogenated polyvinylidene such as PVDC, amorphous nylon or crystalline nylon or combination of both, copolymers of ethylene vinyl alcohol copolymer layer (EVOH), polyolefins, including combinations of two or more of the above layers, and wherein the outer layers consist of structural polymer (e.g. PE, PP or PET).

The disclosure therefore also provides for a flexible container, preferably a multi-chamber container for parenteral or nutritional formulations which may be prepared from any of the before-mentioned flexible films. For example, the container may be in the form of a bag having one or multiple compartments or chambers. The container, such as a bag, may include at least two chambers, but may also contain three, four, five or six or more chambers, and in one preferred embodiment, two or three chambers.

Suitable containers, including soft bags, typically are sterile, non-pyrogenic, single-use, and/or ready-to-use. The multi-chamber containers are particularly useful for holding a parenteral nutrition product for adults, children or neonates and can provide a carbohydrate formulation as disclosed herein in the first chamber, an amino acid formulation as disclosed herein in a second chamber, and a lipid formulation as disclosed herein in a third chamber of the container.

The multi-chamber container may include vertical chambers as disclosed in U.S. Patent Publication No. 2007/0092579. For example, the multi-chamber container may be configured as a bag that includes two, three, four, five or six adjacent chambers or compartments. If desired, frangible barriers or openable seals (e.g., peel seals or frangible seals) are used to separate the chambers of the multi-chamber container. Multi-chamber containers may also comprise three chambers for accommodating a lipid emulsion, a carbohydrate formulation and an amino acid formulation, and further comprise at least one, in certain embodiments two or three smaller chambers which contain, for example, vitamin formulations and/or trace element formulations. In one specific embodiment, the multi-chamber container of the invention has a first chamber containing the lipid emulsion according to the invention, a second chamber containing an amino acid formulation, a third chamber containing a carbohydrate formulation, a fourth chamber containing a vitamin formulation and a fifth chamber containing a trace element formulation.

A multi chamber container or multi chamber bag (MCB) as used in the context of the invention may be designed for the parenteral administration of its reconstituted content after admixing the formulations contained in the respective chambers. Such MCB may have 2, 3, 4, 5, 6 or more chambers. The chambers of said MCB may have the same size or may have different sizes to accommodate various compositions and volumes. The chambers may be designed to contain volumes of from, for ex-ample, 1 to 5 ml, from 5 to 10 ml, from 10 to 50 ml, from 50 to 100 ml, from 100 to 250 ml, from 250 ml to 500 ml, from 500 to 1000 ml, from 1000 to 1500 ml. The MCBs can be designed to have chambers which are located adjacent to each other. The chambers may have various shapes. The chambers can be oriented horizontally and/or vertically to each other. Certain small chambers can be designed to be located within another, larger chamber, wherein, for example, the small chamber which is located within another, larger chamber can be accommodated and fixed into said larger chamber by welding at least one edge of said small chamber in between the weld seam of the surrounding larger chamber.

The openable seals of said multi-chamber containers permit formulations to be separately stored and admixed/reconstituted just prior to administration thereby allowing storage in a single container of formulations which should not be stored as an admixture for an extended period of time. Opening of the seals allows communication between the chambers and mixing of the contents of the respective chambers. The outside seals of the multi-chamber container are strong seals that do not open under the fluid pressure supplied to open the weaker peel seals or frangible seals between the chambers. In some embodiments, the openable seals of the multi-chamber container may be designed to allow for the admixing or reconstitution of only selected chambers of the multi-chamber container, for example, the admixing of the lipid emulsion with the vitamin chamber and the amino acid chamber, if so desired.

The multi-chamber container may be provided with instructions explaining a desired order with which to open the peel seals, so that constituent fluids are mixed in a desired order. The unsealing strengths of the two or more peel seals may be varied to promote the opening of the seals in the desired order. For example, the unsealing strength of the peel seal to be opened first may be ⅓ to ½ of the unsealing strength required to open the peel seal to be opened second.

In embodiments, the container comprises at least a first chamber containing a carbohydrate formulation, a second chamber containing an amino acid formulation, a third chamber containing a lipid formulation, optionally comprises electrolytes and/or vitamins in at least the first, second and/or third chamber, and wherein at least one chamber comprises sodium selenite, selenous acid and/or selenium dioxide in the presence of from 1 ppm to 8 ppm oxygen.

As used herein, amino acid formulations include a sterile, aqueous solution of one or more amino acids and one or more electrolytes. Typically, amino acid formulations include about 2 g to about 10 grams of amino acids per 100 mL of amino acid formulation, such as about 3 grams to about 9 grams and/or about 5 grams to about 7 grams per 100 mL of amino acid formulation. Typical amino acids which are included into amino acid formulations are, for example, isoleucine, leucine, valine, lysine, methionine, phenylalanine, threonine, tryptophan, arginine, histidine, alanine, aspartic acid, cysteine, glutamic acid, glycine, proline, serine, tyrosine, ornithine, and taurine. Further, the content of tyrosine can be increased by adding, for example, a glycyl-tyrosine dipeptide or acetyl-tyrosine (Ac-Tyr). Typically, however, the glycyl-tyrosine dipeptide has improved pharmacokinetics compared to Ac-Tyr, which is more rapidly eliminated by the kidney, resulting in diminished release of tyrosine in the blood.

The amino acid formulation may further include electrolytes. As used herein, electrolytes include sodium, potassium, calcium, magnesium, and/or phosphate ions. For example, the amino acid formulation can include from about 0.1 mmol to about 10 mmol of sodium (e.g., about 3.75 mmol to about 10 mmol of sodium), from about 0.1 mmol to about 10 mmol of potassium (e.g., about 3.75 mmol to about 6.90 mmol of potassium), from about 0.05 mmol to about 1.0 mmol of magnesium (e.g., about 0.05 mmol to about 0.11 mmol and/or about 0.38 mmol to about 0.65 mmol of magnesium), from about 0.1 mmol to about 10 mmol of calcium (e.g., about 1.13 mmol to about 5.10 mmol of calcium), from about 0.1 mmol to about 10 mmol of phosphate (e.g., about 0.94 mmol to about 5.10 mmol of phosphate) and not more than 10 mmol of chloride (e.g., not more than 5.6 mmol of chloride) per 100 mL of amino acid formulation. When calcium and phosphorus are present together in the same heat-sterilized solution, insoluble calcium phosphate precipitation can occur. Using an organic salt of phosphorus such as sodium glycerophosphate 5·H2O or calcium glycerophosphate, calcium and phosphate amounts may be increased without solubility issues and without providing excess sodium or chloride. In the amino acid formulation, sodium may be provided in the form of sodium chloride, calcium may be provided in the form of calcium chloride 2·H2O or calcium gluconate, magnesium may be provided in the form of magnesium acetate 4·H2O or magnesium chloride, and potassium may be provided in the form of potassium acetate.

Carbohydrate formulations provide a supply of calories, typically in the form of glucose. In particular, the carbohydrate formulation provides an amount of carbohydrate sufficient to avoid adverse effects such as hyperglycemia that has been observed in patients receiving parenteral nutrition. Typically, the carbohydrate formulation includes about 20 to 50 grams of glucose per 100 mL of carbohydrate formulation.

Lipid formulations such as mentioned in the context of the present invention herein are an emulsion of an oil phase, a water phase, and an emulsifier that makes the two phases miscible. In case of lipid emulsions, which are to be used as an injectable emulsion for parenteral nutrition, the emulsion must be an oil-in-water (o/w) emulsion. This means that the oil must reside in the internal (or dispersed) phase, while water is the external (or continuous) phase, as the emulsion must be miscible with blood. Lipid emulsion as disclosed herein must therefore also be substantially free of any suspended solids. Of course, the lipid emulsions may contain further components, including, but not limited to, antioxidants, pH modifiers, isotonic agents, vitamins, trace elements and various combinations thereof. An overview over lipid emulsions, their composition and use is provided, for example, in Driscoll, Journal of Parenteral and Enteral Nutrition 2017, 41, 125-134. Further information on the use of lipid emulsions in parenteral nutrition of intensive care patients is provided, for example, in Calder et al, Intensive Care Medicine, 2010, 36(5), 735-749.

The oil phase of the lipid emulsion may include polyunsaturated fatty acids, such as long-chain polyunsaturated fatty acids, which may be present as the free acid, as an ionized or salt form of the free acid, and/or in ester form. Suitable esters of the polyunsaturated fatty acids/long-chain polyunsaturated fatty acids include, but are not limited to, alkyl esters (e.g., methyl esters, ethyl esters, propyl esters, or combinations thereof) and triglyceride esters. In some cases, the long-chain polyunsaturated fatty acid has a structure R(C═O)OR', wherein R is an alkenyl group having at least 17 carbon atoms, at least 19 carbon atoms, at least 21 carbon atoms, or at least 23 carbon atoms, and R' is absent, H, a counter ion, an alkyl group (e.g., methyl, ethyl, or propyl), or a glyceryl group (e.g., R(C═O)OR' is a monoglyceride, a diglyceride, or a triglyceride). Polyunsaturated fatty acids for use in the lipid formulations disclosed herein include, but are not limited to, linoleic acid (LA), arachidonic acid (ARA), α-linolenic acid (ALA), eicosapentaenoic acid (EPA), docosahexaenoic acid (DHA), stearidonic acid (SDA), γ-linolenic acid (GLA), dihomo-γ-linolenic acid (DPA), and docosapentaenoic acid (DPA), particularly, DHA, ARA, and EPA, each of which may be present in free acid form, ionized or salt form, alkyl ester form, and/or triglyceride form. In some cases, the polyunsaturated fatty acids and/or long-chain fatty acids are present in triglyceride form.

Typically, the lipid formulation includes about 5% to about 35% by weight of an oil phase based on the total weight of the lipid emulsion. For example, the oil phase of the lipid emulsion is present in an amount of about 8% to 12%, of about 10% to about 20%, of about 10% to about 15%, of about 15% to about 20%, of about 12% to about 17%, of about 18% to 22% and/or about 20% by weight based on the total weight of the lipid formulation. The oil phase typically and preferably contains, in various amounts depending on the source of the oil, omega-3 fatty acids. The three types of omega-3 fatty acids involved in human metabolism are eicosapentaenoic acid (EPA) and docosahexaenoic acid (DHA), both of which are usually found in marine fish oils and α-linolenic acid (ALA), commonly found in plant oils.

The oil phase and its components can be derived from a single source or different sources (see, for example, Fell et al, Advances in Nutrition, 2015, 6(5), 600-610. Of the plant oils, currently used sources include, but are not limited to, soybean and olive oil as well as coconut or palm kernel oil (medium-chain triglycerides (MCTs)). Another source are algae, including microalgae such as *Crypthecodinium cohnii* and *Schizochytrium* sp., which in some cases serve as the single source of the long-chain polyunsaturated fatty acid docosahexaenoic acid (DHA). Marine oil used in parenteral lipid emulsions is processed from oily fish primarily found in cold water and including, but not limited to, herring, shad and sardines. However, other marine organisms can be used as an oil source, such as, for example, krill, such as Antarctic krill (Euphausia superba Dana). Krill oil, for example, provides for both EPA and DHA, in amounts of up to 35% w/w of the fatty acids. Krill oil as a component of lipid emulsions is considered to have anti-inflammatory properties due to the presence of DHA and EPA and is hypothesized to bind endotoxins (Bonaterra et al: Krill oil-in-water emulsions protects against lipopoly-saccharides-induced proinflammatory activation of macrophages in vitro. Marine Drugs (2017), 15:74).

The lipid emulsions referred to herein may further include additional components, such as surfactants (also referred to as emulsifiers), co-surfactants, isotonic agents, pH adjusters, and antioxidants. Generally, surfactants are added to stabilize emulsions by reducing the interfacial tension between the oil phase and the aqueous phase. Surfactants typically include a hydrophobic part and a hydrophilic part, and the amount of surfactant/emulsifier included in the formulations is determined based on the amount that is needed to achieve a desired level of stabilization of the emulsion. Typically, the amount of surfactant in the lipid formulation is about 0.01% to about 3% by weight based on the total weight of the lipid formulation, for example, about 0.01% to about 2.5%, about 0.01% to about 2.3%, about 0.02% to about 2.2%, about 0.02% to about 2.1%, about 0.02% to about 2%, about 0.05% to about 1.8%, about 0.1% to about 1.6%, about 0.5% to about 1.5%, about 0.8% to about 1.4%, about 0.9% to about 1.3%, about 1% to about 1.2%, and/or about 1.2% by weight. Suitable surfactants and co-surfactants include surfactants that are approved for parenteral use, and include, but are not limited to, phospholipids (e.g., egg phosphatide and soy lecithin), oleate salts, and combinations thereof. Krill oil can also be used as an emulsifier in the lipid emulsion, wherein the lipid emulsion comprises about 0.5 to 2.2 wt % krill oil based on the total weight of the emulsion, and wherein the emulsion is free of egg yolk lecithin (US 2018/0000732 A1). Another exemplary surfactant is lecithin, including both natural and synthetic lecithin, such as lecithins derived from egg, corn or soybean or mixtures there-of. In some cases, lecithin is included in an amount of about 1.2% based on the total weight of the lipid formulation.

In some cases, the lipid emulsion formulation includes a co-surfactant. Typically, the amount of co-surfactant in the lipid formulation is less than the amount of surfactant, and typically the amount of co-surfactant in the formulation is about 0.001% to about 0.6% by weight based on the total weight of the lipid formulation, for example, about 0.001% to about 0.55%, about 0.001% to about 0.525%, about 0.001% to about 0.5%, about 0.005% to about 0.5%, about 0.01% to about 0.4%, about 0.02% to about 0.3%, about 0.03% to about 0.2%, about 0.04% to about 0.1%, and/or about 0.05% to about 0.08%. An exemplary co-surfactant is oleate, such as sodium oleate. In some cases, the lipid formulation includes lecithin and oleate as surfactant and co-surfactant, for example, an in amount of 1.2% lecithin and 0.03% oleate. In some cases, sodium oleate is included in an amount of about 0.03% by weight based on the total weight of the lipid formulation.

Isotonic agents can be added to the lipid emulsions to adjust the osmolarity of the lipid emulsion to a desired level, such as a physiologically acceptable level. Suitable isotonic agents include, but are not limited to, glycerol. Typically, the lipid emulsion formulation has an osmolarity of about 180 to about 300 milliosmols/liter, such as about 190 to about 280 milliosmols/liter, and/or about 200 to about 250 milliosmols/liter. In some cases, the lipid emulsion includes an isotonic agent in an amount of about 1% to about 10% by weight based on the total weight of the lipid formulation, such as about 1% to about 5%, about 1% to about 4%, and/or about 2% to about 3%. In some cases, the lipid emulsion formulation includes about 2% to about 3% by weight of glycerol.

pH modifiers can be added to the lipid emulsions to adjust the pH to a desired level, such as a physiologically acceptable pH for parenteral use. Suitable pH modifiers include, but are not limited to sodium hydroxide and hydrochloric acid. Typically, the lipid emulsion formulation has a pH of about 6 to about 9, such as about 6.1 to about 8.9, about 6.2 to about 8.8, about 6.3 to about 8.7, about 6.4 to about 8.6, about 6.5 to about 8.5, about 6.6 to about 8.4, about 6.7 to about 8.3, about 6.8 to about 8.2, about 6.9 to about 8.1, about 7 to about 8, about 7.1 to about 7.9, about 7.2 to about 7.8, about 7.3 to about 7.7, about 7.4 to about 7.6, about 7, about 7.5, and/or about 8.

The lipid formulations may further include antioxidants. Suitable antioxidants may be pharmaceutically acceptable antioxidants and include, but are not limited to, tocopherols (e.g., gamma tocopherol, delta tocopherol, alpha tocopherol), ascorbyl palmitate, or combinations thereof. In some cases, the lipid emulsion formulation includes an antioxidant in an amount of about 0 to about 200 mg/L, for example, about 10 to about 200 mg/L, about 40 to about 150 mg/L, about 50 to about 120 mg/L, about 75 to about 100 mg/L antioxidant(s), such as vitamin E.

The aqueous (or water) phase of all intravenous lipid emulsions must conform to the pharmacopeial requirements that make it suitable for injection, that is, the water must be sterile water for injection.

The lipid emulsions can be prepared according to generally known processes (see, for example, Hippalgaonkar et al, AAPS PharmSciTech 2010, 11(4), 1526-1540 or WO 2019/197198 A1)). Generally, water soluble and oil-soluble ingredients are dissolved in the aqueous phase and oil phase, respectively.

If not defined otherwise herein, all terms used in the context of the present invention are to be interpreted according to the understanding of a person skilled in the art.

FIGURES

The invention is further described by the following figures. These are not intended to limit the scope of the invention but represent preferred embodiments of aspects of the invention provided for greater illustration of the invention described herein.

EXAMPLES

Figure 1:
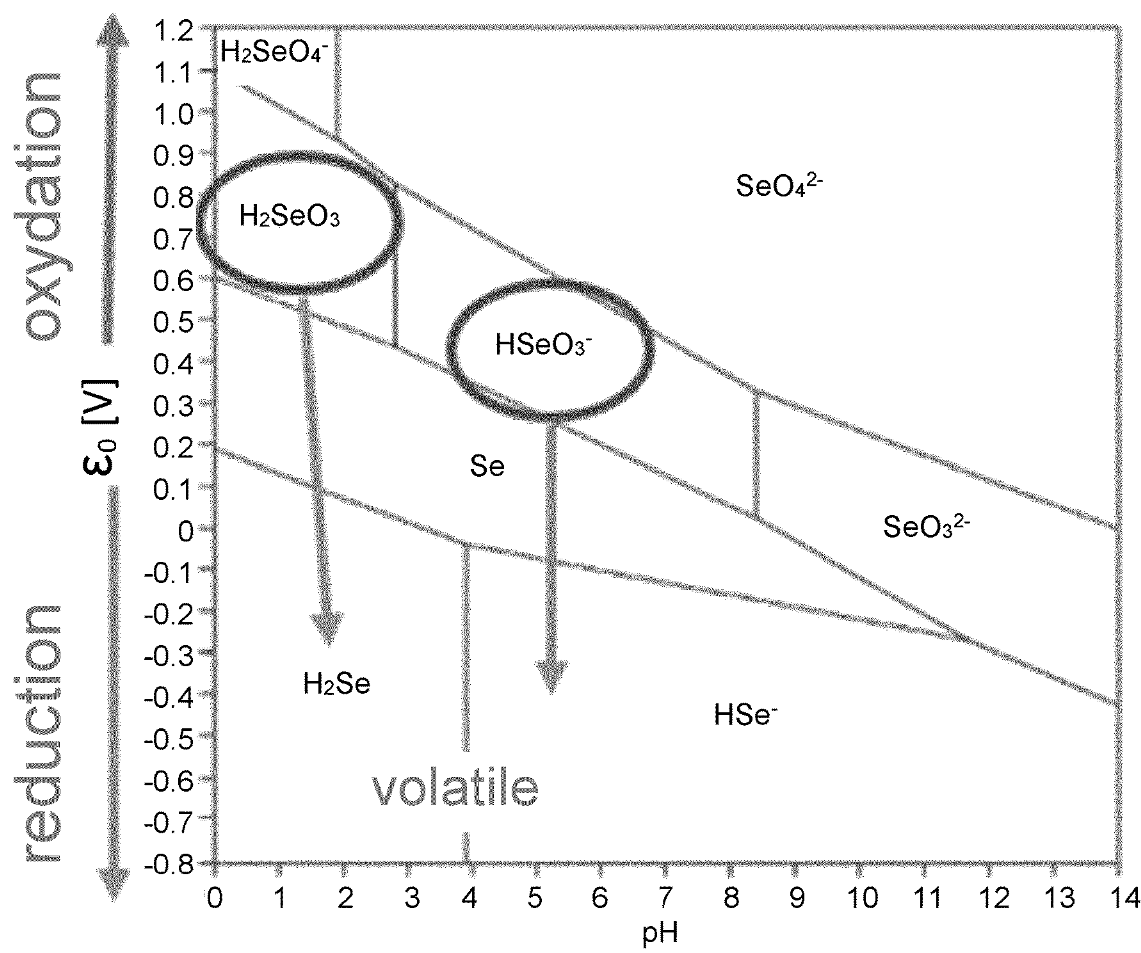
FIG. 1: pH/redox diagram illustrating the transformation/reduction of $SeO_3$ into volatile species in a media totally free of oxygen.

The invention is further described by the following examples. These are not intended to limit the scope of the invention but represent preferred embodiments of aspects of the invention provided for greater illustration of the invention described herein.

Example 1: Lab-Scale Manufacturing of a Selenium Containing Solution for Parenteral Nutrition or Administration For preparing a selenium containing solution according to the invention the required amount of organic acid is dissolved in water for injection and the pH of the solution is adjusted to the target pH±0.5 with NaOH or HCl, as needed. In a next step the selenium as sodium selenite, selenium dioxide or selenous acid is introduced into the solution and stirred or agitated until complete dissolution. Afterwards, the pH is again controlled and, if needed, finally adjusted to the target pH±0.2 with NaOH or HCl. Oxygen can then be introduced either by exposing the solution to the atmosphere under stirring or agitation, followed by measuring the DO and flushing the solution with nitrogen if the DO is too high and needs to be adjusted to lower values, flushing with nitrogen is stopped, accordingly, when the target oxygen concentration is reached.

Alternatively, the solution is initially flushed with nitrogen to remove essentially all of the dissolved oxygen and oxygen is then added e.g. by stirring the solution or by bubbling oxygen into the solution under constant measurement until the desired amount of oxygen is dissolved. Once the desired DO has been achieved, the solution is filled into a container under constant control of the DO and then closed/sealed. The solution can then undergo terminal heat sterilization. Besides, the remaining gas headspace present in the bag after filling can be totally removed, partially removed or replaced by oxygen or nitrogen in define amount to reach the target level of DO.

Example 2: Lab-Scale Manufacturing of a Multi Trace Element Solution for Parenteral Nutrition or Administration Containing Selenium For preparing a multi trace element selenium containing solution for parenteral nutrition/administration the required amount of organic acid is dissolved in water for injection and the pH of the solution is adjusted to the target pH±0.5 with NaOH or HCl, as needed. In a next step the required amount of each trace element weighed in and added to the solution under constant stirring or agitation until complete dissolution. If, for certain trace elements, the required quantity is too low for weighing in the required amount, an intermediate concentrated solution can be previously prepared. A given volume of this intermediate solution will then be added to the final solution to reach the target concentration. Afterwards, the pH is again controlled and, if needed, finally adjusted to the target pH±0.2 with NaOH or HCl. Oxygen can then be introduced either by exposing the solution to the atmosphere under stirring or agitation, followed by measuring the DO and flushing the solution with nitrogen if the DO is too high and needs to be adjusted to lower values, flushing with nitrogen is stopped, accordingly, when the target oxygen concentration is reached.

Alternatively, the solution is initially flushed with nitrogen to remove essentially all of the dissolved oxygen and oxygen is then added e.g. by stirring the solution or by bubbling oxygen into the solution under constant measurement until the desired amount of oxygen is dissolved. Once the desired DO has been achieved, the solution is filled into a container under constant control of the DO and then closed/sealed. The solution can then undergo terminal heat sterilization. Besides, the remaining gas headspace present in the bag after filling can be totally removed, partially removed or replaced by oxygen or nitrogen in define amount to reach the target level of DO.

Example 3: Methods for Determining the DO Concentration

As mentioned in the description of the invention, various methods can be used to determine the DO content of a given solution. Generally, electrochemical or optical sensors are used for determining the DO concentration according to the invention. A preferred method comprises using a fiber-optic oxygen meter such as MICROX TX3, which is a single-channel, temperature-compensated oxygen meter with fiber-optic trace oxygen microsensors based on a glass fiber (e.g. 140 μm). The optical oxygen microsensors (also called optodes) do not consume oxygen, their signal does not depend of the flow rate of the sample, the diameter of the microsensor tip is e.g. <50 μm, they measure oxygen in both liquid and gas phase and they have an on-line temperature compensation of the oxygen content. For data visualization during measurements, the oxygen meter is connected to a LCD & Data-Logger Unit.

The oxygen measure and adjustment are based on an equilibrium between exposure to nitrogen and oxygen containing gases during the mixing and filling steps of the process. An acute and regular monitoring of the solution DO throughout these process steps allows to control the oxygen level within the final container. Besides, the headspace of the bag can be filled with a specific volume of nitrogen or oxygen to reach the final targeted level of DO.

Example 4: Evaluation of Various Factors on the Stability of Selenite

A full factorial DoE was designed to evaluate the impact of five factors on the stability of Selenite:

Container material: an interaction between Selenite and plastic bags material was previously highlighted. To evaluate this factor a neutral material i.e. glass bottles was used as a comparison to plastic bags.

pH of the solution: all previous studies were conducted at pH<3.5 to ensure stability of Fe. A comparison with a native pH>7 obtained by simple dilution of Selenite into MilliQ water allowed to evaluate the impact of this parameter.

Sterilization: the terminal heat sterilization conducted on samples may initiate degradative chemical reactions by heat exposure. Unsterilized VS sterilized samples were compared regarding Selenite stability to assess the impact of this process step.

Storage temperature: accelerated stability studies are classically conducted at 40° C. However, selenite might be sensitive to it and a comparison with samples stored at 5° C. was conducted.

Dissolved oxygen content: oxygen is involved in many redox reactions most of the time deleterious for macro and micronutrients (particularly vitamins). To assess the impact of this parameter on Selenite stability, solutions of Selenite were flushed either with oxygen (up to saturation at about 8 ppm) or with nitrogen (DO<0.5 ppm).

All combinations of factors were produced and stored under appropriate conditions for 6 months. They were then submitted to several tests to evaluate the impact of each factor on several responses.

The following readouts were performed in order to assess the impact of the factors listed above:

Se assay to evaluate the degradation of Selenium.

Visual inspection of the samples to detect any precipitate, particles or discoloration.

pH measurement to evaluate the evolution of sample pH after 6 months storage.

Dissolved oxygen measurement to evaluate the evolution of the dissolved oxygen after 6 months of storage.

Redox potential measurement as Selenite is engaged into different Se redox couples the information on redox potential of the solution might help to understand the stability of this element.

For almost all responses studied, a same group of samples presented a different behavior than the rest of them. Observations are detailed in Table 3 below.

TABLE 3

Assessment of the different readouts visual inspection, pH, Dissolved oxygen, delta redox potential and Se assay for samples flushed with nitrogen and stored in plastic bags versus other samples (i.e. all samples flushed with oxygen + samples flushed with nitrogen and stored in glass bottles).

| Response | Samples flushed with Nitrogen and stored in plastic bags | Other samples i.e. all samples flushed with oxygen + samples flushed with nitrogen and stored in glass bottles |
|---|---|---|
| Visual inspection | No particles nor discoloration but strong egg-smell at the opening of the overpouch | Particles dust like in the glass bottles. Nothing detected in plastic bags samples |
| pH | No significant variation of pH after 6 months storage | No significant variation of pH after 6 months storage |
| Dissolved oxygen | About 0 ppm of oxygen detected after 6 months | All samples present significant content of oxygen (>1.5 ppm) even samples in glass bottles flushed with nitrogen during manufacturing |
| Delta redox potential | Significant decrease of redox potential during the 5 minutes measure (up to −400 mV) witness of a reductive reaction | No significant variation during the 5 minutes measure or slight increase witness of a neutral or oxydative behaviour |
| Se assay | Significant degradation of Se (i.e. more than 10% degradation after 6 months) | No significant degradation of Se (i.e. +/−10% variation after 6 months) |

These observations allowed to conclude that in samples flushed with nitrogen and stored in oxygen-permeable plastic bags the degradation of selenium observed is most probably due to a reduction of Selenite $SeO_3$ in $H_2Se$/HSe—, a volatile form of Se known to present a bad smell similar to sulfuric gas. The pH/redox diagram presented in FIG. 1 illustrates the transformation of $SeO_3$ in these volatile species in a medium totally free of oxygen.

Example 5: Impact of DO on Selenium Stability

The impact of oxygen seems of major importance in the stability of Selenite. Indeed, the few amounts of oxygen that penetrates into the solution initially flushed with nitrogen but stored in glass bottles certainly blocked the reduction reaction and allowed to maintain the stability of $SeO_3$. To confirm this hypothesis, a regression test was performed between Se assay results and log(dissolved oxygen results). Only sterilized samples stored at 40° C. were considered as the sterilization and storage at high temperature seem to both increase the Se degradation. Indeed, most reaction kinetics are accelerated by heat explaining that samples not sterilized and kept at 5° C. for 6 months do not present a degradation as important as for samples sterilized and stored at 40° C.

Figure 2:
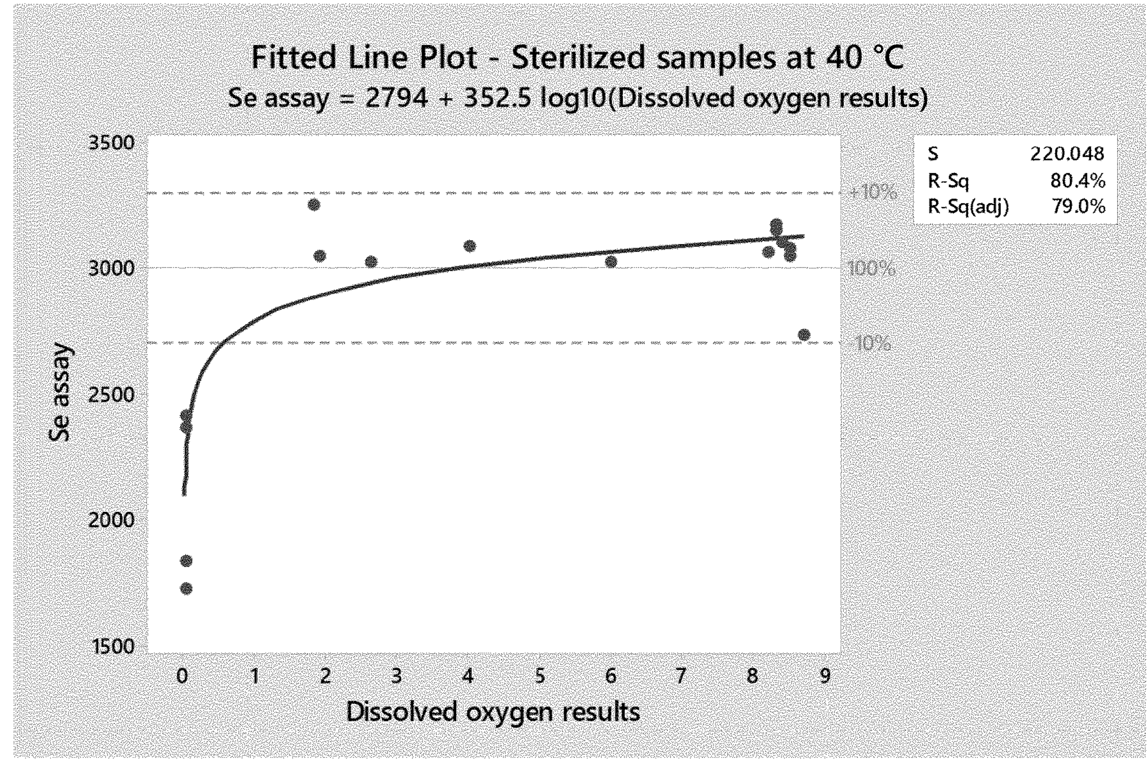
FIG. 2: Fitted line plot showing a 80% fit between Se dosage and log oxygen content (ppm).

The fitted line plot presented in FIG. 2 shows a 80% fit between Se dosage and log oxygen content. Considering a +/−5% analytical variability and the few samples used for this regression test it can be considered as significantly representative. Dissolved oxygen content is so the most impacting parameter and CQA in the stability of Selenium. As shown by FIG. 2, low oxygen amounts of around 0.5 ppm can be sufficient to ensure the stability of Selenite in solution, no saturation would be required.

The presence of oxygen promotes selenite stability. To ensure that it is not deleterious to another TE the stability of a mix of the 9 TE of interest (i.e. Zn, Cu, Cr, Mo, Mn, Fe, I, F & Se) was evaluated at pH 2.2 with 200 mM of malic acid (to ensure Iodide stability) and stored in a glass bottle (so containing about 3 ppm of dissolved oxygen). The solution was heat sterilized and stored 6 months at 40° C. or 5° C. (T6M 40° C. and T6M 5° C., respectively). Recovered concentrations of the respective trace elements after 6 months at the two temperatures are summarized in the Table 4.

TABLE 4

Initial (theoretical) concentration of the respective TE and the concentrations recovered after 6 months at 5° C. or 40° C. and corresponding percentage of the recovered TE are indicated.

| | Theoretical concentration | | | | |
|---|---|---|---|---|---|
| | | T6 M 5° C. | | T6 M 40° C. | |
| TE | μg/L | μg/L | % | μg/L | % |
| Zn | 203561 | 158347 | 77.8% | 171822 | 84.4% |
| Cu | 12057 | 9784 | 81.1% | 10504 | 87.1% |
| Mn | 2204 | 1838 | 83.4% | 1949 | 88.4% |
| F | 39959 | NA | 94% | NA | 88% |
| I | 4029 | 3167 | 78.6% | 3401 | 84.4% |
| Se | 2806 | 2446 | 87.2% | 2461 | 87.7% |
| Mo | 817 | 653 | 79.9% | 707 | 86.6% |
| Cr | 396 | 306 | 77.3% | 329 | 83.1% |
| Fe | 40116 | 31842 | 79.4% | 34190 | 85.2% |

For all TE recoveries are around 80-90% at both temperatures. An excessive dilution might explain this lower than expected recoveries, but it is known that at 5° C. samples should be stable and so it can be considered as a reference. Comparison of the two samples shows that none of the TE was degraded significantly after 6 months storage at 40° C. It confirms the hypothesis that selenite stable in the presence of few ppm of dissolved oxygen. This presence of oxygen is not deleterious for the stability of the other TE.

It can be attested that oxygen introduction would not be a problem in manufacturing. For example, instead of flushing the solution with nitrogen as it was done so far, it should be kept under ambient air allowing a sufficient amount of oxygen to be dissolved into the solution. This oxygen content could be monitored at any time as an in-process control. During filling, sterilization and storage steps, the dissolved oxygen could be maintained in the solution by using a bag material impermeable to oxygen. Such materials do neither allow any oxygen entering the bag nor being removed out of the bag (even in contact with an oxygen absorber). This way the oxygen would remain entrapped within the TE solution and avoid Se degradation all along the shelf life of the product.

Example 6: Tests Performed with Oxygen Semi-Permeable and Oxygen Impermeable Barrier Films Tests have been performed with two different films, an oxygen semipermeable-film (EU2-S) and an oxygen impermeable film (EU2-F).

The semi-permeable film is a co-extruded film having the following structure: PP|Tie|PA|Tie|PP/SEBS/LLDPE. Therein, “PP” refers to polypropylene, “PA” refers to polyamide, “SEBS” refers to styrene-ethylene-butylene-styrene block copolymer, and “LLDPE” refers to linear low-density polyethylene. “Tie” refers to special adhesive polymers or “tie resins” which are typically polyethylene copolymers of polar and nonpolar repeat units and with or without functional reactive groups, which are used to improve adhesion between the main layers of the multi-layer film. The oxygen barrier of the film is provided by the polyamide layer (~50 cc/m$^2$/day). Corresponding films have been described, for example, in US20100247935A1. The semipermeable film allows some oxygen to pass.

The oxygen-impermeable film is made from a coextruded polyolefinic material laminated to a polyester with a deposit of silicon oxide to provide an oxygen barrier, i.e. the oxygen barrier provided by PET-SiOx is <1 cc/m$^2$/day.

In the tests described in Examples 6 and 7, 1 dd/25 ml of sodium selenite was present at a pH of 3.0+/−0.2. 100 mM malic acid was present as well in a 50 ml mono-bag having one port-tube, wherein the bag was either made of semi-permeable or oxygen-impermeable material as described above.

Figure 4:
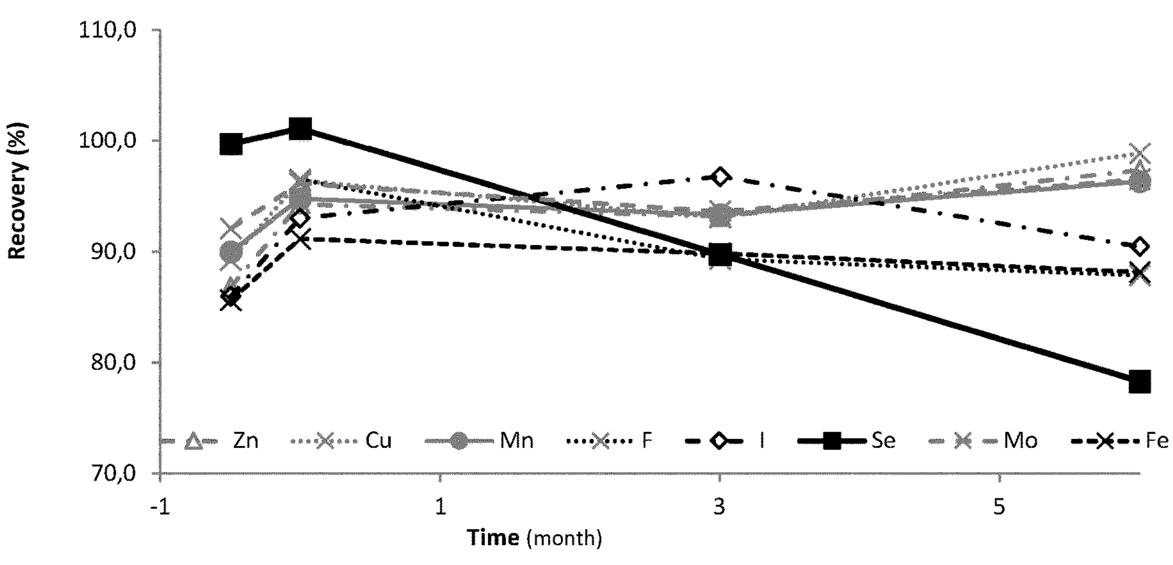
FIG. 4: Analysis of influence of (A) an oxygen semipermeable bag material and (B) an oxygen-impermeable bag material on selenite stability.
Figure 4:
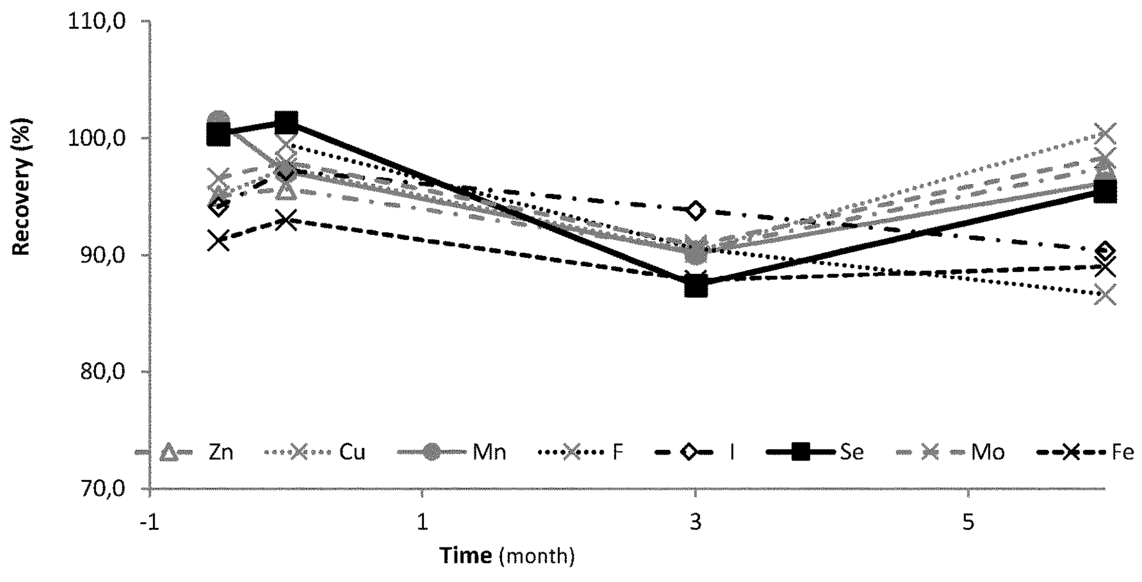

After mixing, the respective solution was flushed with nitrogen to arrive at a DO of below 0.5 ppm. A headspace of 10 ml ambient air was left in said 50 ml bag. After filling the oxygen was allowed to reach saturation (about 8 ppm, see FIG. 3). The respective container was sealed and wrapped in an oxygen impermeable aluminum overpouch to which an oxygen absorber was added. The respective container was then submitted to moist heat sterilization. The following results were observed:

As shown in FIG. 4, it was found that selenite, in the EU-2S batch (semi-permeable), fell below 80% recovery after about 5 months (FIG. 4A). It can be concluded that oxygen is drawn from the solution because of the oxygen absorber present on the outer pouch and the presence of a semi-permeable primary film which allows oxygen to pass. In the EU2-F bag (oxygen-impermeable), this did not happen because of the oxygen barrier film (FIG. 4B). Selenite was retained and stayed above the threshold of 80% recovery. So, an oxygen barrier film is advantageous to ensure stability of the selenite containing solution.

Figure 3:
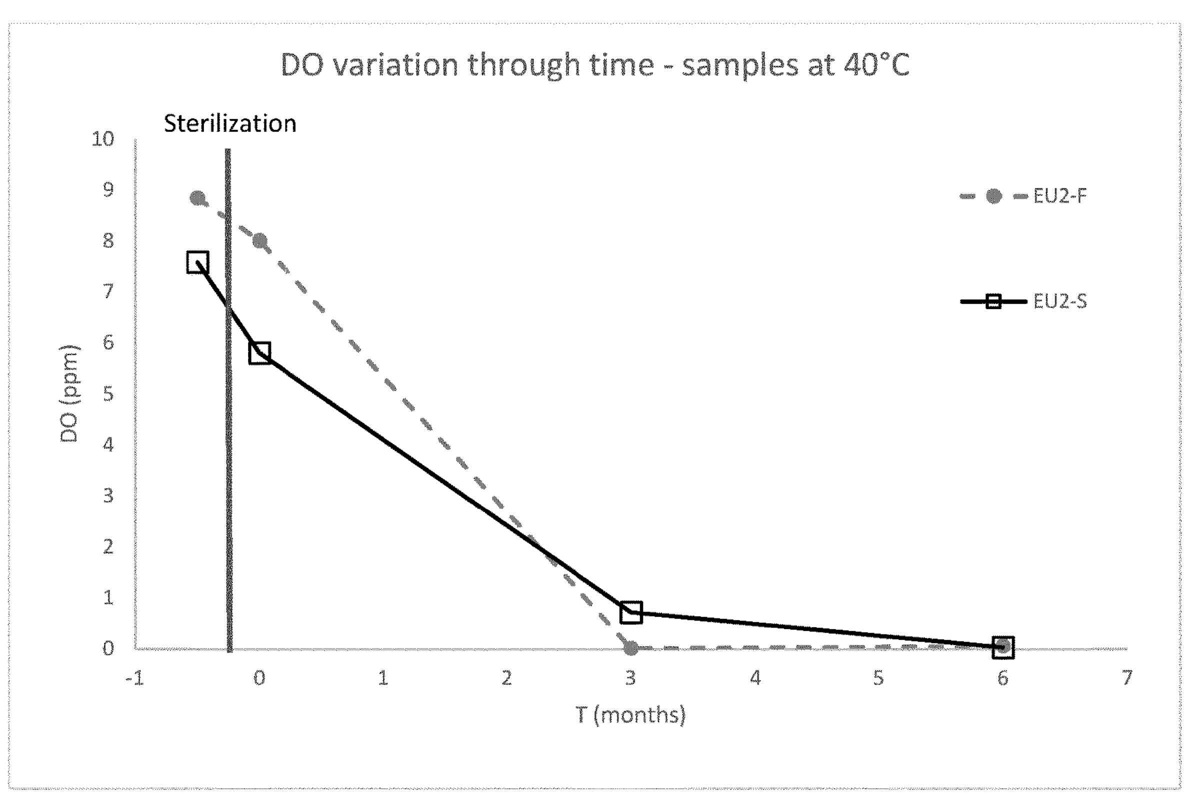
FIG. 3: Variation of DO over time in bag made of oxygen semipermeable (EU2-S) and oxygen impermeable (EU2-F) films.

Importantly, as shown in FIG. 3, the DO fell from saturation to essentially 0 ppm DO in both cases even though this process was faster in case of the EU2S semi-permeable film and the effect of the oxygen absorber.

Accordingly, the DO content decreased even though an oxygen barrier film was used. It was found that some components in the solution, including, for example, other trace elements or malic acid, seem to consume the DO, even though it is no longer lost by permeating through the film. The presence of malic acid, for example, was found to have an influence on the DO consumption in such scenario. Without wanting to be bound by theory, it is assumed, that the redox potential in the solution favors the consumption of (reaction with) oxygen.

Importantly, as long as the DO concentration does not decrease below 0.5 ppm, the selenite remains stable and can be recovered with a rate of above 80% over 5 months. This is achieved by having a DO, at the time of filling, of above 6 ppm, preferably between 6-8 ppm (essentially up to saturation).

Example 7: Relevance of Headspace

In this example, Milli-Q water was used that was kept at ambient air and was, accordingly, saturated with oxygen. The solution volume used was 15 ml.

Figure 5:
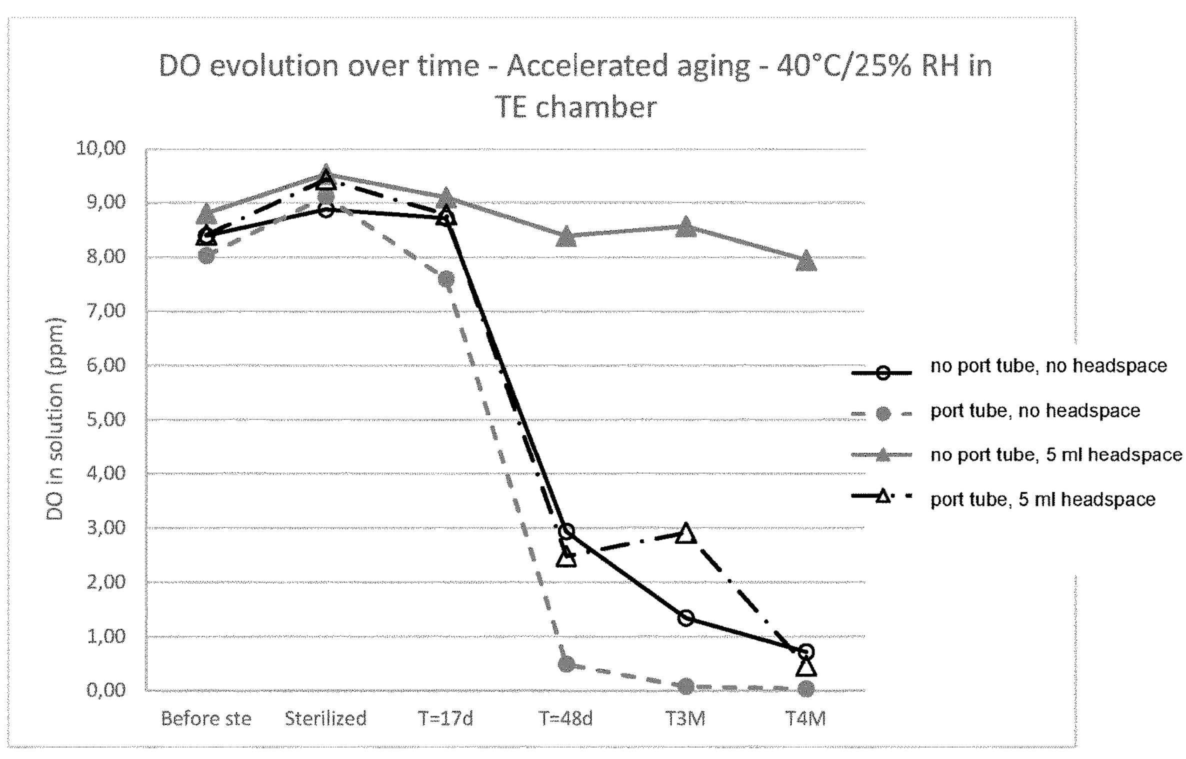
FIG. 5: Analysis of the influence of headspace and port tube on DO in combination with an oxygen-impermeable bag.
Figure 5:
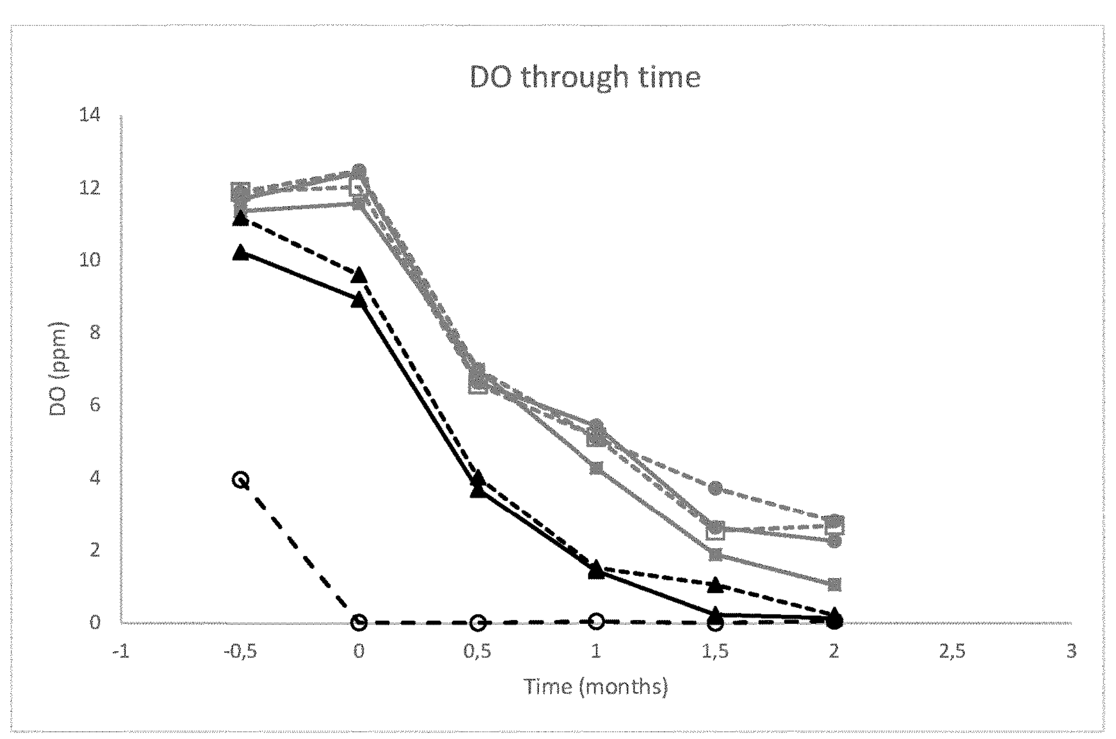

As shown in FIG. 5A, it was found that without headspace, even when the oxygen impermeable film was used, DO content rapidly fell below the threshold of 0.5 ppm (in contrast to the above setup, where headspace was included). It could thus be shown that the headspace filled with ambient air provides for an "oxygen stock" which replaces oxygen that is lost from the container due to the presence of a port tube. Oxygen from the headspace slowly gets dissolved in the solution until equilibrium is reached. Accordingly, the DO can be kept above 0.5 ppm over time if a headspace is present. Without headspace (filled grey circles), the selenite cannot be stabilized due to DO loss over time.

Accordingly, the port tube is another aspect which may contribute to DO loss, as the port tube must be sealed between the film layers and this portion of the seal is difficult to make completely oxygen tight. Accordingly, it is advantageous to improve the oxygen tightness of the port tube used in a setting as described herein, or, where possible, to completely remove the port tube, if possible. In FIG. 5A, it becomes obvious that without headspace and without port tube (open black circles) the DO is higher over time compared to a port tube being present (closed grey circle), and that a headspace of 5 ml, for example, cannot fully compensate the loss over the port tube (open black triangle). Preferably, there is a headspace and no port tube, if possible, for stabilizing a selenite comprising solution in an oxygen barrier bag. In such setting, the DO can basically be maintained (filled grey triangle).

FIG. 5B focuses on the volume of the headspace. As can be seen and as discussed above, a headspace is required for maintaining required DO levels in compositions where oxygen present in the solution at the time of filling is consumed by components present in the solution (DO is consumed by redox reaction in the solution, see open black circles, dashed line) or otherwise lost from the container. 2 ml headspace per 25 ml container/chamber volume or 15 ml solution is not fully sufficient either (black triangles). With 6 ml headspace the threshold of 0.5 ppm can about be met even if a port tube is present (grey square, continues line) and is fully sufficient if a port tube is absent (grey square, dashed line). Best results are obtained with a headspace of 10 ml per 15 ml solution of the chamber/container (filled grey circles, continuous line), even if port tube is present (filled grey circles, dashed line).

The invention claimed is:

1. A medical product for preventing or correcting selenium deficiency in a patient, the medical product comprising an oxygen impermeable flexible container and further comprising a solution provided in the oxygen impermeable flexible container, wherein the solution comprises at least one selenium compound in the form of Se(IV) selected from the group consisting of sodium selenite, selenous acid and selenium dioxide, and wherein the solution comprises dissolved oxygen (DO) in a concentration from 0.5 ppm to 8 ppm.

2. The medical product according to claim 1, wherein the DO stabilizes the at least one selenium compound in the solution for at least three months when stored at a temperature between 1 and 50° C.

3. The medical product according to claim 1, wherein the DO stabilizes the at least one selenium compound in the solution for at least 6 months at a temperature of from about 18° C. to 25° C.

4. The medical product according to claim 1, wherein the solution is a sterilized solution.

5. The medical product according to claim 1, wherein the concentration of DO is from 0.5 ppm to 2 ppm throughout shelf life of the medical product.

6. The medical product according to claim 1, wherein the concentration of DO is from 1 ppm to 2 ppm.

7. The medical product according to claim 1, wherein the oxygen impermeable flexible container comprises a headspace with a gas composition comprising oxygen.

8. The medical product according to claim 1, wherein the at least one selenium compound comprises sodium selenite.

9. The medical product according to claim 1, wherein the solution has an acidic pH in a range of from 1 to 4.

10. The medical product according to claim 1, wherein the solution comprises an organic acid selected from the group consisting of malic acid, tartaric acid, citric acid, maleic acid and fumaric acid, wherein the concentration of the organic acid is in the range of from 100 mM to 400 mM.

11. The medical product according to claim 1, wherein the solution comprises malic acid.

12. The medical product according to claim 1, wherein the solution does not comprise macronutrients selected from the group consisting of carbohydrates, proteins and lipids, and wherein the solution does not comprise any other nutrients.

13. The medical product according to claim 1, wherein the solution comprises—at least one additional trace element selected from the group consisting of zinc, iron, copper, manganese, chromium, iodine, fluoride and molybdenum.

14. The medical product according to claim 1, wherein the solution is administered parenterally.

15. The medical product according to claim 1, wherein the at least one selenium compound is in an amount corresponding to 10-200 μg.

16. A medical product for preventing or correcting selenium deficiency in a patient according to claim 1, wherein the oxygen impermeable flexible container is a multi chamber container and wherein the solution is contained in a chamber of the multi chamber container.

17. The medical product according to claim 16, wherein the oxygen impermeable flexible container comprises a first chamber containing a carbohydrate formulation, a second chamber containing an amino acid formulation, a third chamber containing a lipid formulation, wherein at least one of the first chamber, the second chamber, or the third chamber includes the solution.

18. The medical product according to claim 16, wherein the oxygen impermeable flexible container comprises a first chamber containing a carbohydrate formulation, a second chamber containing an amino acid formulation, a third chamber containing a lipid formulation, and a fourth chamber containing the solution.

19. The medical product according to claim 16, wherein the at least one selenium compound comprises sodium selenite.

20. A sterilized solution for parenteral administration comprising at least one selenium compound in the form of Se(IV) selected from the group consisting of sodium selenite, selenous acid and selenium dioxide, wherein the sterilized solution is formulated to prevent or correct selenium deficiency in a patient, wherein the solution comprises dissolved oxygen (DO), and wherein the sterilized solution is contained in an oxygen impermeable flexible container.

* * * * *